United States Patent
Kelly et al.

(10) Patent No.: US 12,262,962 B2
(45) Date of Patent: Apr. 1, 2025

(54) SYSTEMS AND METHODS FOR ADVANCED MEDICAL DEVICE PLACEMENT AND USAGE

(71) Applicants: Dignity Health, San Francisco, CA (US); Arizona Board of Regents on Behalf of Arizona State University, Scottsdale, AZ (US)

(72) Inventors: Brian Kelly, Tempe, AZ (US); Anna Newcomb, Chandler, AZ (US); William Langenbach, Phoenix, AZ (US); Kirsten Jefferys, Norman, OK (US); Luis Manuel Tumialan, Paradise Valley, AZ (US); James Abbas, Scottsdale, AZ (US)

(73) Assignees: Dignity Health, San Francisco, CA (US); Arizona Board of Regents on Behalf of Arizona State University, Scottsdale, AZ (US)

( * ) Notice: Subject to any disclaimer, the term of this patent is extended or adjusted under 35 U.S.C. 154(b) by 447 days.

(21) Appl. No.: 16/488,920

(22) PCT Filed: Feb. 27, 2018

(86) PCT No.: PCT/US2018/019966
§ 371 (c)(1),
(2) Date: Aug. 26, 2019

(87) PCT Pub. No.: WO2018/157135
PCT Pub. Date: Aug. 30, 2018

(65) Prior Publication Data
US 2020/0008888 A1    Jan. 9, 2020

Related U.S. Application Data

(60) Provisional application No. 62/463,765, filed on Feb. 27, 2017.

(51) Int. Cl.
*A61B 34/00* (2016.01)
*A61B 17/70* (2006.01)
(Continued)

(52) U.S. Cl.
CPC .......... *A61B 34/25* (2016.02); *A61B 17/7082* (2013.01); *A61B 90/06* (2016.02);
(Continued)

(58) Field of Classification Search
CPC .......................... A61B 90/06; A61B 2090/067
See application file for complete search history.

(56) References Cited

U.S. PATENT DOCUMENTS

| 7,580,743 B2 | 8/2009 | Bourlion et al. |
| 8,249,696 B2 | 8/2012 | Fisher et al. |

(Continued)

FOREIGN PATENT DOCUMENTS

| WO | 2007136784 A2 | 11/2007 |
| WO | 2015171697 A1 | 11/2015 |

OTHER PUBLICATIONS

International Searching Authority. International Search Report and Written Opinion for application PCT/US2018/019966, 13 pages. Mailed on May 11, 2018.

(Continued)

*Primary Examiner* — Andrew Yang
(74) *Attorney, Agent, or Firm* — QUARLES & BRADY LLP

(57) ABSTRACT

Systems and methods for providing orientation data to a user during a medical procedure performed on a subject are provided. The system can include a medical device, an electrical component and a display device. The medical device is configured to engage a portion the subject and includes a handle. The electrical component is disposed within the handle and is configured to generate data related
(Continued)

to an orientation of the medical device during the medical procedure. The display device is physically separate from the medical device and in communication the electrical component. The display device also includes a processor configured to receive and process the data related to the orientation of the medical device, and display information related to the orientation of the medical device to the user based on the data.

19 Claims, 12 Drawing Sheets

(51) Int. Cl.
  *A61B 90/00* (2016.01)
  *A61B 90/30* (2016.01)
(52) U.S. Cl.
  CPC ........ *A61B 90/30* (2016.02); *A61B 2034/254* (2016.02); *A61B 2090/067* (2016.02); *A61B 2560/0223* (2013.01); *A61B 2562/0219* (2013.01)

(56) References Cited

U.S. PATENT DOCUMENTS

| | | | |
|---|---|---|---|
| 8,419,746 B2 | 4/2013 | Bourlion et al. | |
| 9,119,572 B2 | 9/2015 | Gorek et al. | |
| 9,241,742 B2 | 1/2016 | Stad | |
| 9,414,940 B2 | 8/2016 | Stein et al. | |
| 2003/0199882 A1 | 10/2003 | Gorek | |
| 2008/0167650 A1* | 7/2008 | Joshi | C01B 7/14 606/41 |
| 2008/0249355 A1 | 10/2008 | Birnkrant et al. | |
| 2010/0087823 A1 | 4/2010 | Kondrashov | |
| 2013/0079678 A1* | 3/2013 | Stein | A61B 5/103 600/594 |
| 2013/0218166 A1 | 8/2013 | Elmore | |
| 2013/0253599 A1 | 9/2013 | Gorek et al. | |
| 2015/0238204 A1 | 8/2015 | Stone | |
| 2016/0213383 A1 | 7/2016 | van der Walt et al. | |
| 2016/0235481 A1 | 8/2016 | Dorman | |
| 2016/0239610 A1 | 8/2016 | Andersen | |
| 2017/0007328 A1 | 1/2017 | Cattin et al. | |

OTHER PUBLICATIONS

Jost, G. F., et al. "iPod Touch-Assisted Instrumentation of the Spine A Technical Report." Operative Neurosurgery 73.2 (2013): ons233-ons237.

European Patent Office, Communication pursuant to Article 94(3) EPC issued Aug. 8, 2024 for corresponding European Patent Application No. 18757525.3 [6 pgs].

* cited by examiner

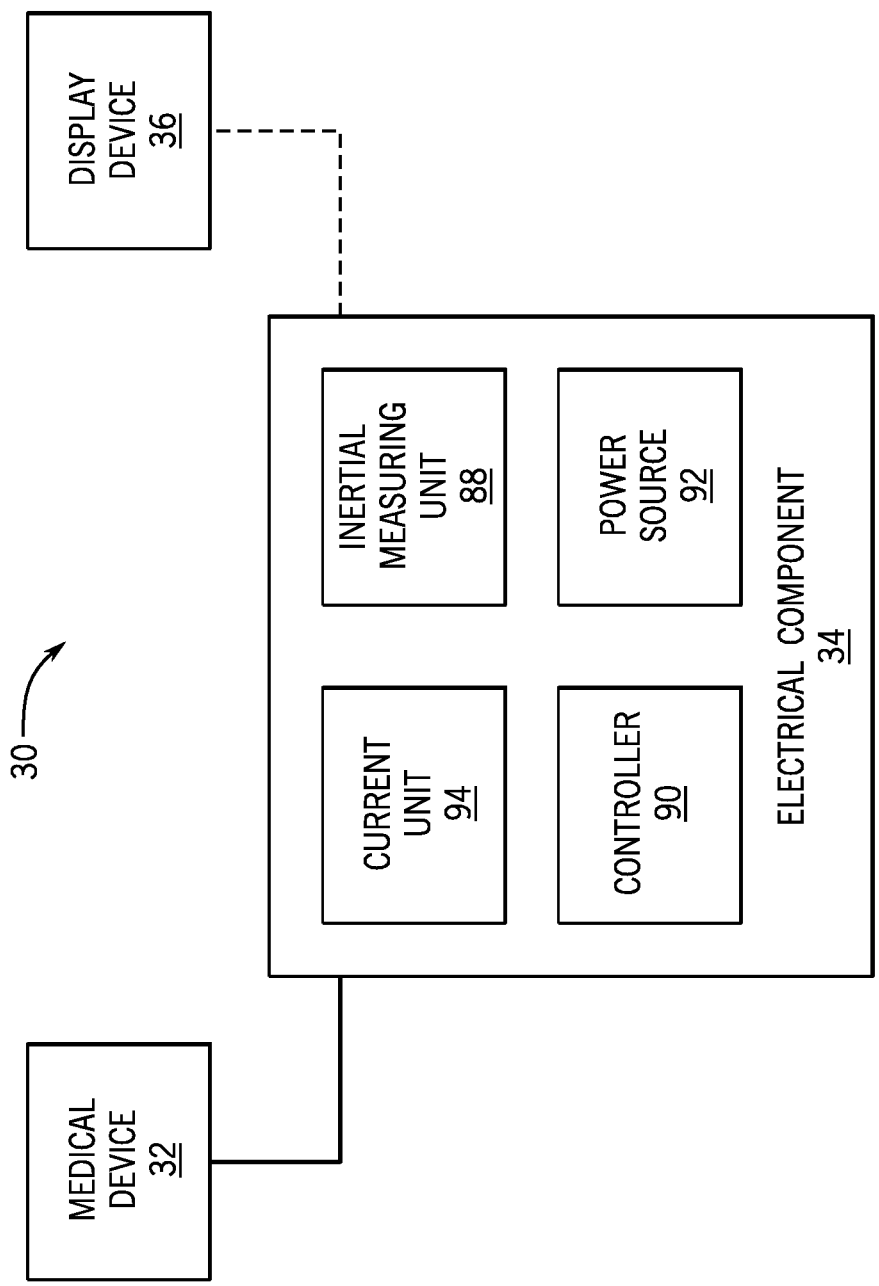

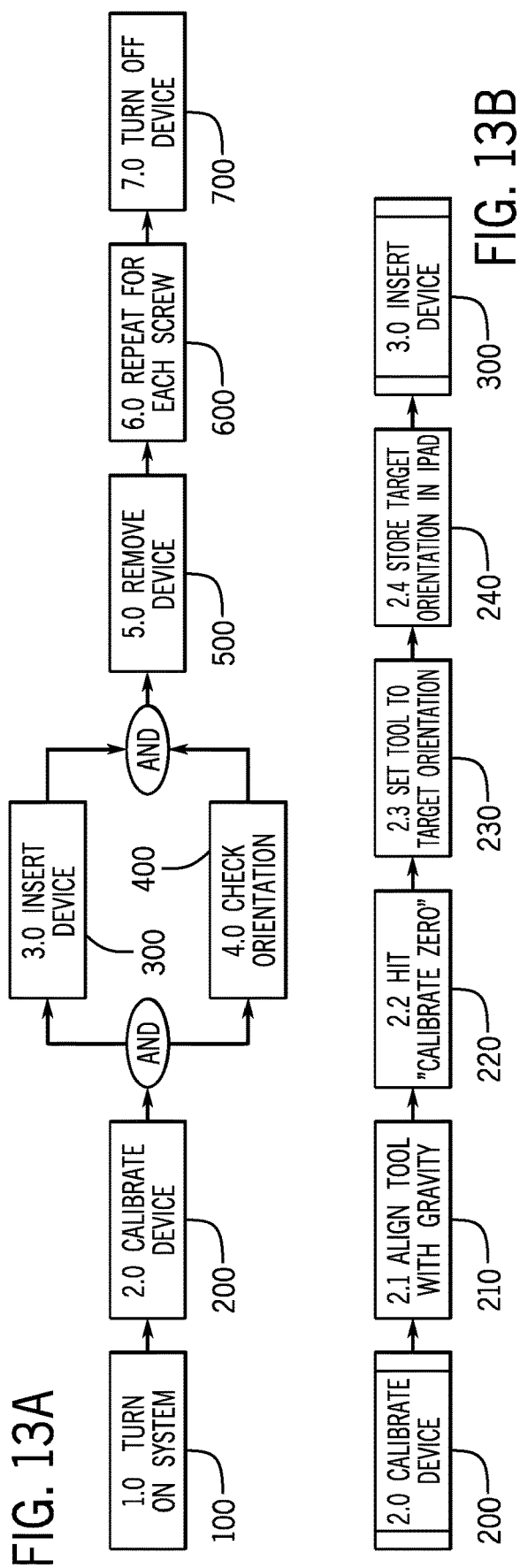
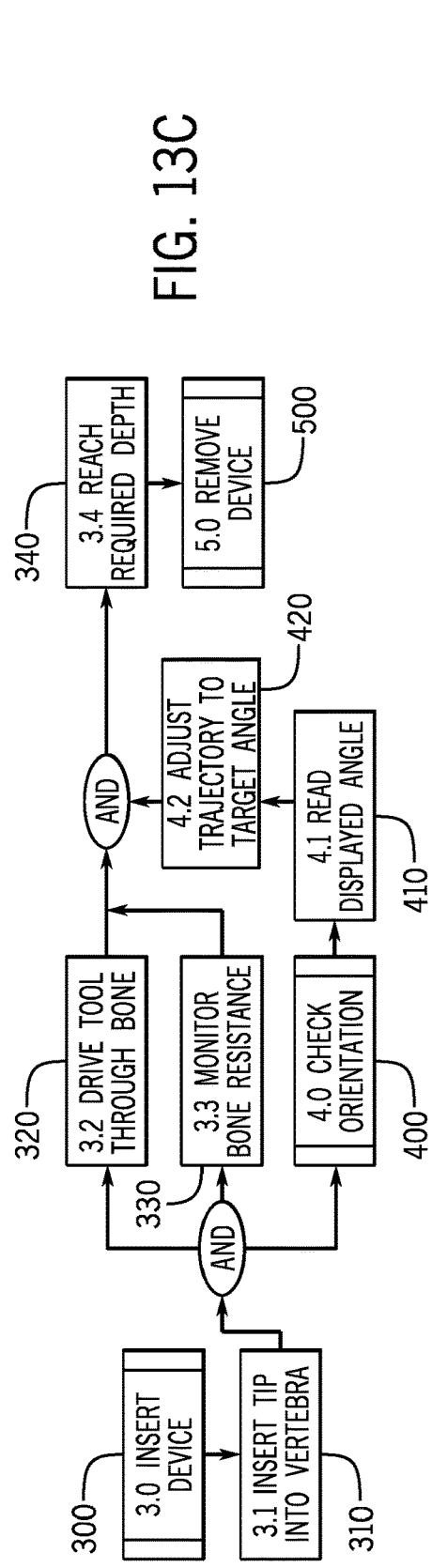
FIG. 13A
FIG. 13B
FIG. 13C

SYSTEMS AND METHODS FOR ADVANCED MEDICAL DEVICE PLACEMENT AND USAGE

CROSS REFERENCE TO RELATED APPLICATIONS

This application is a U.S. National Stage of PCT Application No. PCT/US2018/019966 filed on Feb. 27, 2018 which claims the benefit of U.S. Provisional Patent Application No. 62/463,765 filed on Feb. 27, 2017, the entire contents of which are incorporated herein by reference.

FIELD

Embodiments of the present systems and methods can be employed to detect and display real-time and/or near real-time position, angulation, and/or orientation data for a medical device in use by a medical professional.

BACKGROUND

Spinal fusion is one of the most common invasive inpatient procedures in the United States and may be performed for various reasons, such as trauma recovery, scoliosis and posture correction, and alleviation of nerve pain due to vertebral deformation. Between 1998 and 2008, hospital discharges related to spinal fusions rose from 175,000 to 400,000 per year. Furthermore, this procedure is predicted to keep growing in the foreseeable future due to the increasing population of aging middle-aged to elderly adults in the United States.

However, spinal fusions put a burden on the U.S. healthcare system. These types of interventions are the fifth most expensive surgical procedure, generally exceeding $27,000 per surgery as of February 2014. As these are one of the most expensive surgeries in the U.S., devices have been produced to aid surgeons so that such procedures more effectively relieve nerve pain, stabilize the spine, and/or shape the spine into a healthy alignment. In other words, devices have been produced to increase the effectiveness of the procedure and thereby reduce the need for costly corrective surgeries or treatment. Yet these devices tend to be costly themselves, and many cannot be reused, thus compounding procedure-related expenses.

For example, the current standard of care for spinal fusion procedures includes using a screw-and-rod system to immobilize two or more spinal vertebrae to stabilize the spine. Each vertebra that is immobilized requires two bone screws to act as anchor points for rods that then span a length of a segment to be fused. The most widely used spinal screw placement method involves freehand placement of the screw into a pedicle of each vertebra along preoperatively calculated angles. In particular, this method involves making a guide hole or cannula, by freehand, with a pedicle probe or pedicle finder, widening the hole with a spinal tap, then inserting the screw into the guide hole. For example, FIG. 1A illustrates correct formation of a guide hole 10, that is, positioned directly through a pedicle 12 of a vertebra 14.

However, using the freehand method, surgeons may be prone to perforating either the medial or lateral walls of the pedicle and injuring the spinal cord, arteries, and/or secondary nervous and cardiovascular structures. For example, as shown in FIG. 1B, a surgeon attempting to form a guide hole 16 in a pedicle 12 may perforate the medial wall 18 of the vertebra 14 (or the lateral wall 20, though not shown in FIG. 1B), thereby potentially causing damage to the patient. Misplaced guide holes and screws, like that shown in FIG. 1B, occur in 10-20% of spinal fusion procedures, and often require corrective surgeries and hospital re-admissions. As such, there is a need to increase the accuracy of screw placement in these procedures.

Surgeons routinely employ certain practices to improve the accuracy of the freehand method. For example, some surgeons use a form of radiological imaging to observe screw placement during intermediate points of the screw insertion procedure. In another example, a surgeon may use a metal probe to feel the walls of the guide hole to check for pedicle breaches. In yet another example, a surgeon may insert a device through the guide hole, pass an electrical current through the device, and then monitor the spinal cord for a corresponding signal (e.g., indicating that the device has breached a pedicle and contacted the spine). While these and other methods exist and may be effective at increasing screw placement rate from about 80% to about 95%, such conventional methods subject the patient and surgeon to additional radiation exposure, and conventional devices can be very costly and are generally only for one-time use.

Therefore, there is a need for a cost-effective system and method that can increase the effectiveness of the traditional freehand method of spinal screw placement.

SUMMARY

Embodiments of the present invention provide systems and methods for providing guidance to a user during a medical procedure, such as a spinal fusion procedure, by providing visual feedback to the user relating to medical device placement angles in real time or near real time. The present systems and methods can provide such guidance in a cost-effective manner that decreases operation time, improves medical device placement accuracy, and reduces radiation exposure compared to conventional freehand methods.

In some embodiments, a system for providing orientation data to a user during a medical procedure performed on a subject is provided. The system can include a medical device, an electrical component and a display device. The medical device is configured to engage a portion the subject and includes a handle. The electrical component is disposed within the handle and is configured to generate data related to an orientation of the medical device during the medical procedure. The display device is physically separate from the medical device and in communication the electrical component. The display device also includes a processor configured to receive and process the data related to the orientation of the medical device, and display the information related to the orientation of the medical device to the user based on the data.

In some embodiments, a pedicle angle finder system to provide guidance to a user during a medical procedure performed on a subject is provided. The system can include a medical device, an electrical component, and a display device. The medical device includes a handle with an internal cavity, and a shaft coupled to the handle and configured to engage a pedicle of the subject during the medical procedure. The electrical component is removably positioned within the internal cavity and configured to generate data related to a medial angle and a sagittal angle of the handle during the medical procedure. The display device is in wireless communication with the electrical component and includes a processor configured to receive and process the data from the electrical component and display information related to the medial and sagittal angle of the handle to the user based on the data.

In some embodiments, a method of providing angular guidance to a user during a medical procedure performed on a subject using a system comprising a medical device, an electrical component, and a display device is provided. The method includes coupling the electrical component to the medical device, establishing a wireless connection between the electrical component and the display device, and generating data, via the electrical component, related to a medial angle and a sagittal angle of the medical device during the medical procedure. The method also includes wirelessly communicating the data from the electrical component to the display device, displaying information related to the data to the user via the display device, and repeating these steps as the medical device is moved relative to the subject until the medical procedure is complete. The method further includes removing the electrical component from the medical device.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 12 is another schematic view of a system for advanced medical device placement and guidance according to some embodiments.

FIG. 13 is a flow diagram of a method for advanced medical device placement and guidance, according to some embodiments.

Corresponding reference characters indicate corresponding elements among the view of the drawings. The headings used in the figures should not be interpreted to limit the scope of the claims.

DETAILED DESCRIPTION

Figure 1A:
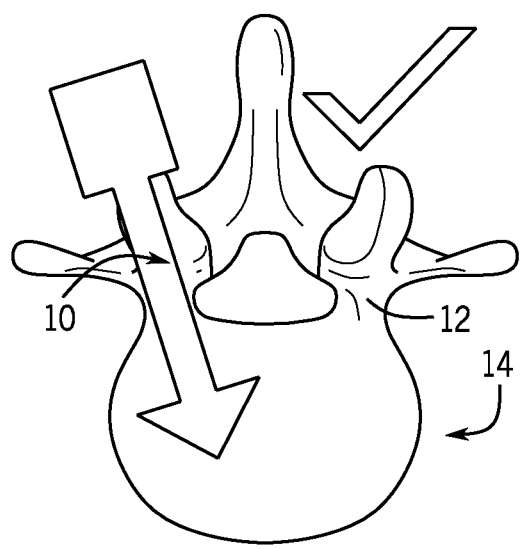
FIG. 1A illustrates correct guide-hole placement during a spinal fusion procedure, where the guide hole is formed through the pedicle of a vertebra and does not perforate the medial or lateral walls of the pedicle.
Figure 1B:
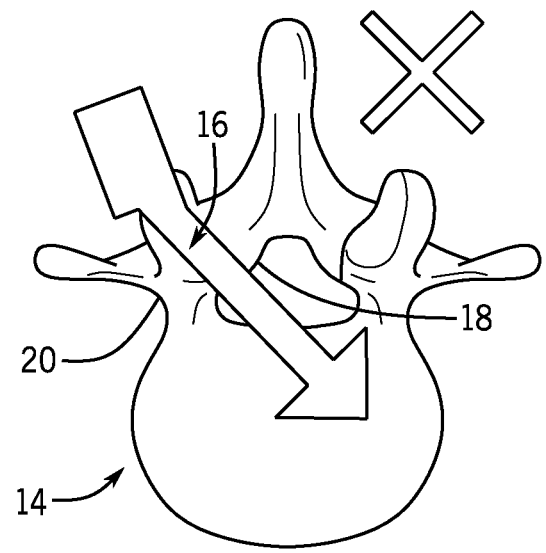
FIG. 1B illustrates an incorrect guide-hole placement during a spinal fusion procedure, where the guide hole is incorrectly formed so that a wall of the pedicle is perforated.

Before the present invention is described in further detail, it is to be understood that the invention is not limited to the particular aspects described. It is also to be understood that the terminology used herein is for the purpose of describing particular aspects only, and is not intended to be limiting. The scope of the present invention will be limited only by the claims. As used herein, the singular forms "a", "an", and "the" include plural aspects unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Aspects referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10.

Generally, embodiments of the invention provide systems and methods for providing guidance to a user, such as a surgeon or other medical professional, during a medical or otherwise health-related procedure. More specifically, the systems and methods can be used by a user that desires guidance information while positioning one or more medical devices during a medical procedure. Such guidance information can include information regarding a particular angle of approach, orientation, trajectory, placement, and/or other information relating to the one or more medical devices. In some embodiments, the systems and methods can be used in an osteotomy-related procedure.

Furthermore, in some embodiments, the systems and methods can be used by a neurosurgeon in the course of performing a neurologically relevant procedure, such as, but not limited to, a spinal fusion procedure (e.g., to assist spinal screw placement) or other spine-related surgery. For example, the systems and methods can be used to assist in the process of spinal screw placement during such procedures without increasing radiation exposure or surgeon workload. The systems and methods can use angle-detecting circuitry to indicate, to the surgeon, a current orientation of a medical tool in real time or near real time.

Figure 2:
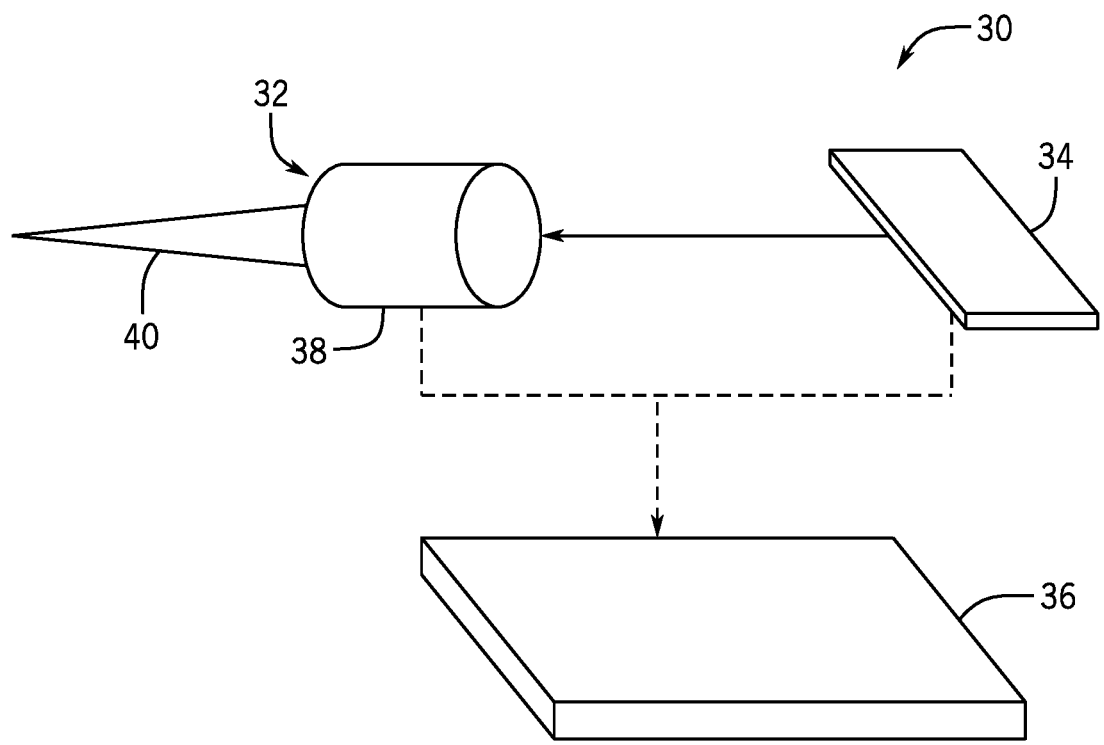
FIG. 2 is a schematic view of a system for advanced medical device placement and guidance according to some embodiments.

FIG. 2 illustrates a schematic view of a system 30 for advanced medical device placement and guidance, according to some embodiments. As shown in FIG. 2, the system 30 can include a medical device 32, at least one electrical component 34, and a display device 36. Generally, the medical device 32 can be used by a user during a medical procedure based on guidance from the display device 36. For example, the electrical component 34 can be coupled to, supported by, or otherwise engaged with the medical device 32 and can be configured to gather or generate one or more types of data related to the operation or positioning of the medical device 32 during the medical procedure. The electrical component 34 can further be configured to communicate such data to the display device 36. The display device 36 can then display information to the user related to the received data so that the user can gain real-time or near real-time guidance on the relative or actual location of the medical device 32.

The system 30 and, in particular, the medical device 32 can comprise a plurality of different configurations. More specifically, the medical device 32 can be configured in the form of any device that can be employed with the electrical component 34 and the display device 36 to provide a user with angular, position, and/or orientation data during a medical procedure. As such, specific components of the medical device 32 can be at least partially related to a need fulfilled by the particular configuration of the medical device 32. By way of example, the medical device 32 can be configured for use in medical procedures such as, but not limited to, osteotomy-related procedures, such as spinal fusions, embolization procedures, and/or pain-management procedures.

According to a first use example, in some embodiments, the medical device 32 can be generally configured as a pedicle finder (e.g., as part of a pedicle angle finder system 30). When configured as such, the medical device 32 can be used by a surgeon, such as a neurosurgeon, to create guide holes or cannula through a pedicle of one or more vertebrae of a subject (e.g., a patient). These guide holes can receive screws for a procedure, such as a spinal fusion surgery. More specifically, the screws can be part of a rod-and-screw system that fixes adjacent vertebrae in place to immobilize a segment of the subject's spine to be fused. In other embodiments, the medical device 32 can be configured as other relevant devices, such as a pedicle screwdriver or any other device that may be required for an osteotomy-related procedure or any other procedure for which angular or position feedback could be beneficial.

In another use example, in some embodiments, the medical device 32 can be configured for use with other medically relevant procedures, such as embolization therapies (e.g., embolization of the liver to treat hepatic cancer) or pain-management therapies. In such embodiments, the medical device 32 can be generally configured in a needle-like configuration, or another type of configuration that engages the human body. When configured as such, the medical device 32 can be used to deliver or inject a substance into a target area. In an example pain management procedure, the medical device 32, can be a needle-like configuration containing pain-management medication (such as analgesics). The medical device 32 can be precisely directed to a subject's area of need, such as the vertebral and/or sacral foramen, using angular data generated and provided to the user via the system 30, thus permitting the user to more accurately and effectively inject the pain-management medication into the area of need.

FIGS. 3A-5 illustrate an implementation of the system 30, according to some embodiments, including the medical device 32, the electrical component 34, and the display device 36. Generally, the embodiment of FIGS. 3A-5 provides a functional pedicle finder. However, while the system 30 of FIGS. 3A-5 is illustrated and described herein with respect to pedicle finders (and/or pedicle screwdrivers), it should be noted that the principles and concepts may be applied to any other medical device configurations for use in other medical procedures.

Figure 3A:
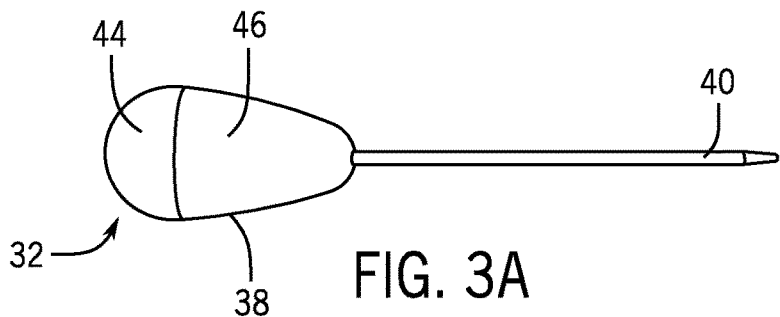
FIG. 3A is a top view of a medical device of some embodiments of the system of FIG. 2.
Figure 3B:
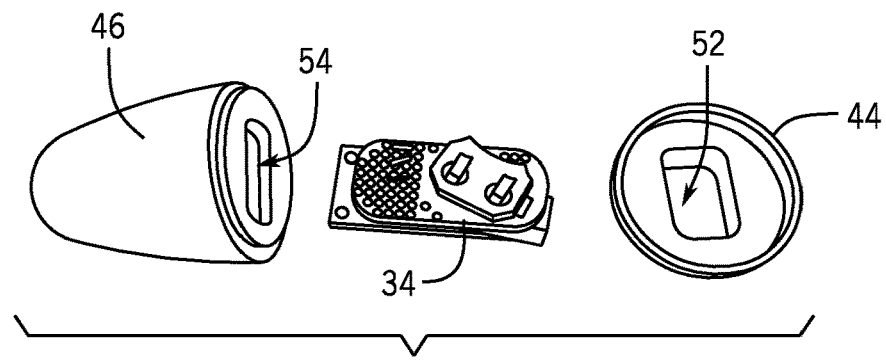
FIG. 3B is top view of an opened handle of the medical device of FIG. 3A.

In some embodiments, as shown in FIG. 3A, the medical device 32 comprises a handle 38 and a shaft 40. The handle 38 can be configured and arranged to be engaged or held by the user (e.g., a surgeon) and the shaft 40 can be configured and arranged to engage a portion of a body of a subject (e.g., a patient) during a medical procedure. For example, the shaft 40 can be configured to be driven into the pedicle of a vertebra of the subject to create a guide hole for a screw to be placed in a spinal fusion procedure. As such, the handle 38 can be held by the user and the user can apply pressure through the handle 38 to cause the shaft 40 to penetrate the pedicle.

Figure 4A:
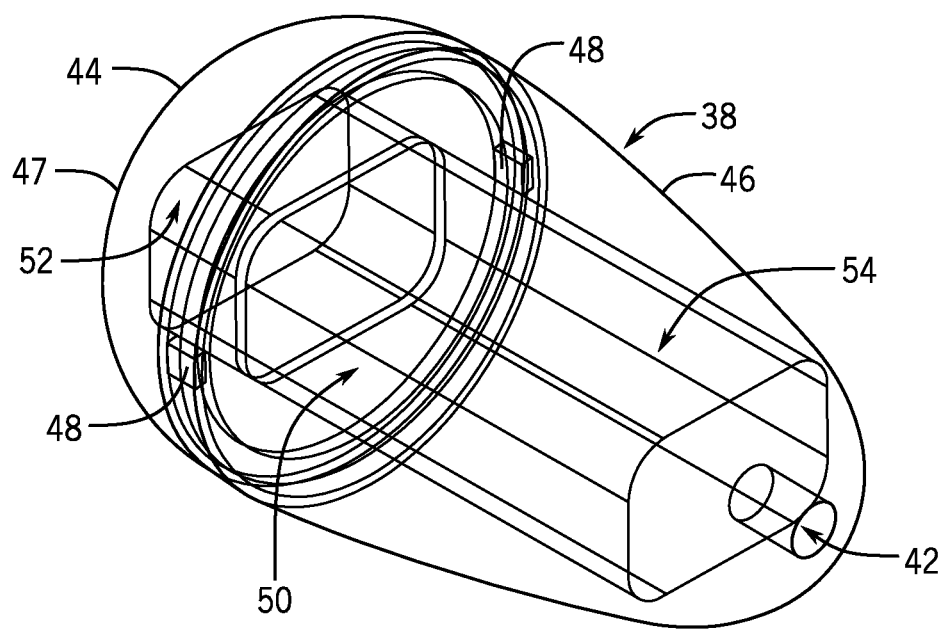
FIG. 4A is a perspective transparent view of a handle of a medical device of some embodiments of the system of FIG. 2.
Figure 4B:
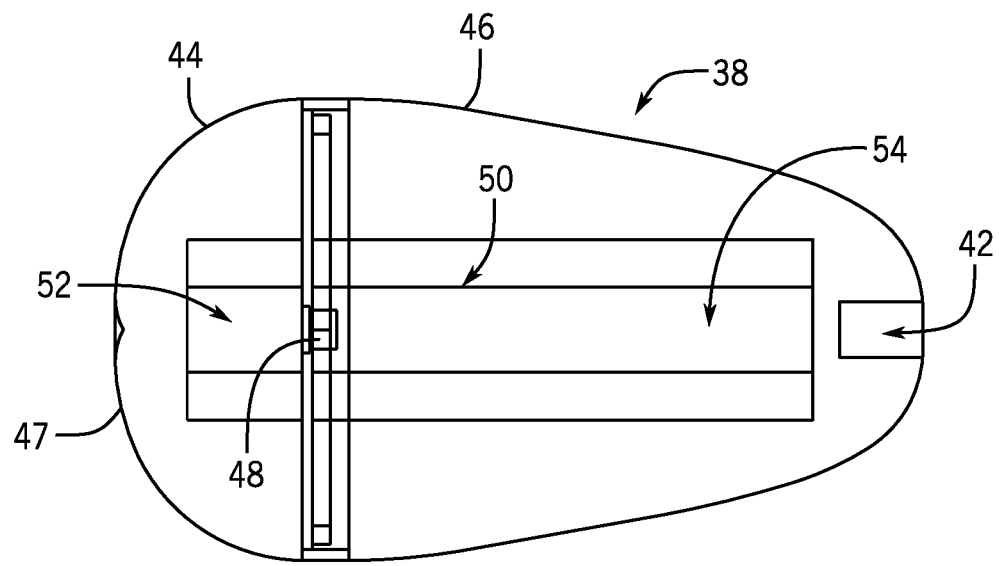
FIG. 4B is a cross-sectional transparent view of the handle of FIG. 4A.
Figure 5A:
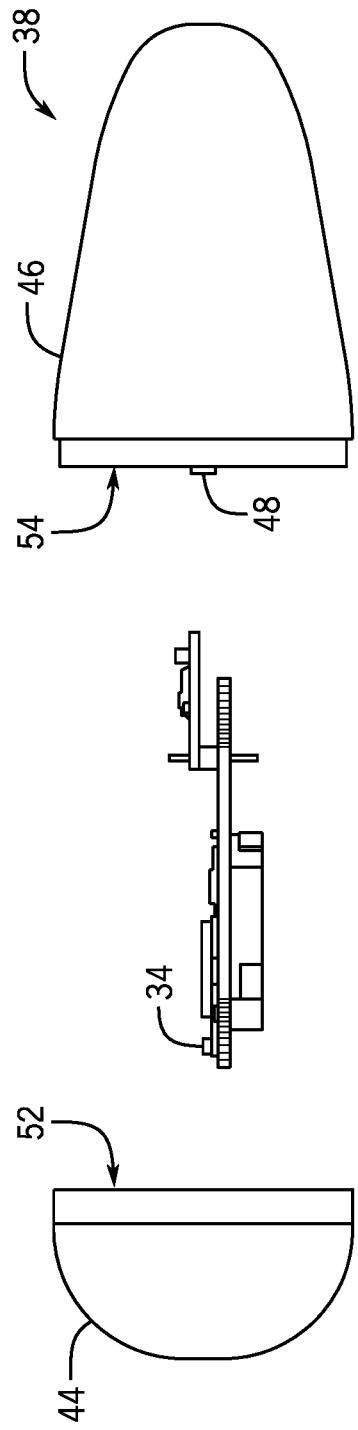
FIG. 5A is an exploded side view of the handle of FIG. 4A and an electrical component of some embodiments of the system.
Figure 5B:
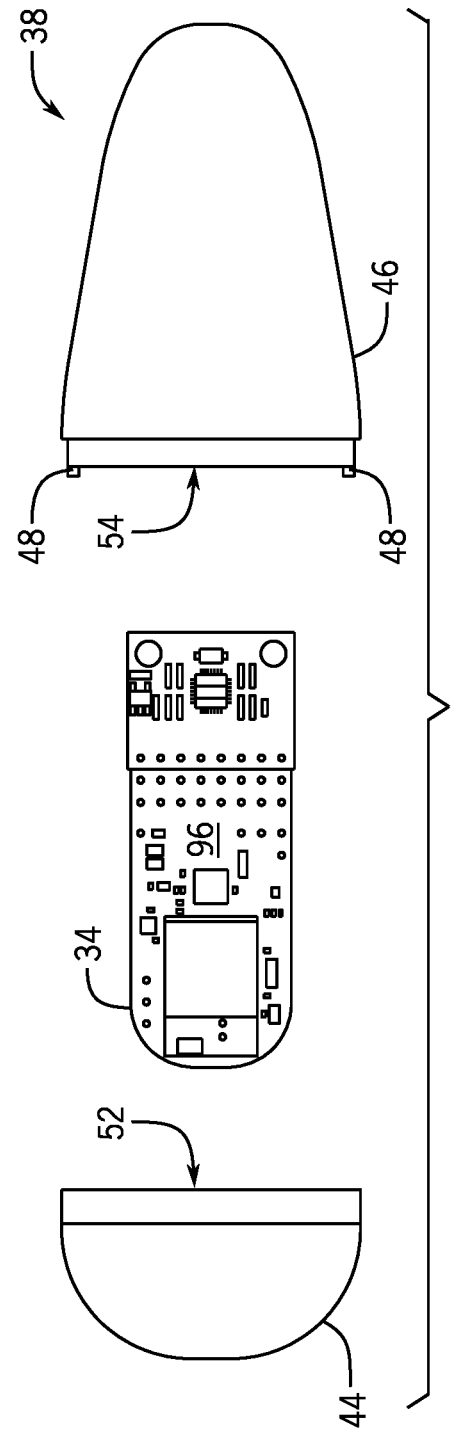
FIG. 5B is a top side view of the handle and the electrical component of FIG. 5A.

Generally, the handle 38 can be coupled to or integral with the shaft 40. For example, in some embodiments, as shown in FIGS. 4A and 4B, the handle 38 can define a shaft aperture 42 configured to receive a portion of the shaft 40. In one embodiment, the shaft aperture 42 can be formed as a blind hole in the handle 38. Additionally, in some embodiments, the shaft aperture 42 can comprise threading (not shown) that is configured to engage mated threading on the shaft 40 (not shown) so that the shaft 40 can be screwed and unscrewed with respect to the handle 38. In other embodiments, the shaft aperture 42 can be sized to receive a portion of the shaft 40 so that the shaft 40 will remain positioned within the shaft aperture 42 and coupled to the handle 38, for example, via a press fit or other suitable coupling method, until the user desires to remove the shaft 40.

In another example, in some embodiments, the handle 38 and the shaft 40 can be irreversibly coupled together and/or formed as a single, integral element. In one implementation, the shaft aperture 42 can include an adhesive substance so that when the shaft 40 is introduced into the shaft aperture 42, the two elements become partially or completely inseparable (e.g., without significant intervention by a user). In other implementations, the handle 38 and the shaft 40 can be formed as a single unit by conventional processes (such as, but not limited to, molding, extruding, or 3D printing). For example, in one embodiment, the handle 38 and the shaft 40 can comprise a substantially unitary piece of surgical-grade stainless steel. However, other materials may be contemplated in some embodiments of the handle 38 and/or the shaft 40, such as polyethylene terephthalate, high density polyethylene, high-impact polystyrene, or other suitable materials.

As shown in FIG. 3A, the handle 38 can be substantially egg-shaped or generally ellipsoidal-shaped to provide a comfortable feel for the user. In other embodiments, however, the handle 38 can comprise any shape and configuration desired by the user. Furthermore, in some embodiments, the handle 38 can comprise one or more pieces. For example, as shown in FIGS. 3A-3B, 4A-4B, and 5A-5B, the handle 38 can include a first member 44 and a second member 46. In some embodiments, the first member 44 can include a substantially smooth or ribbed surface 47 configured to be engaged by the user during a medical procedure. For example, during the procedure, the user's palm can engage the surface 47 to drive the shaft 40 into a pedicle. Additionally, as shown in FIGS. 4A-4B, the second member 46 can include the shaft aperture 22.

Generally, the first and second members 44, 46 can be removably coupled together to form the handle 38. For example, in one embodiment, one or both of the first and second members 44, 46 can comprise one or more hooks or flanges 48 that can engage mating flanges 48 or other structures (not shown) on the opposite member 46, 44 to couple together the first and second members 44, 46. Additionally or alternatively, the first and second members 44, 46 can each comprise a threaded structure so that the first and second members 44, 46 can be screwed and unscrewed relative to one another. In yet other embodiments, the first and second members 44, 46 can be removably coupled to each other via another suitable coupling method.

As shown in FIGS. 4A-4B, the handle 38 can include a cavity 50 sized to house the electrical component 34. More specifically, as shown in FIGS. 3B-5B, the first member 44 can define a first member cavity 52 and the second member 46 can define a second member cavity 54. The first member cavity 52 and the second member cavity 54 can be sized and configured to receive the electrical component 34 when the first member 44 and the second member 46 are coupled together. For example, upon assembly of the first member 44 and the second member 46 (e.g., via engagement of the flanges 48), the first member cavity 52 can substantially or completely align with the second member cavity 54 to provide a substantially continuous cavity 50, as shown in FIGS. 4A-4B, configured to receive and support the electrical component 34. Furthermore, the first member 44 and the second member 46 can be coupled together in a way to substantial seal the cavity 50 from outside elements. In this manner, the electrical component 34 can be securely supported within the cavity 50 during a medical procedure and segregated from any potential contaminating debris and fluids (e.g., to ensure proper functioning of the electrical component 34).

Accordingly, the electrical component 34 can be completely or at least partially disposed within a portion of the medical device 32. In some embodiments, the cavity 50 can be sized so that the electrical component 34 fits snugly inside with minimal movement during use of the medical device 32. Moreover, in some embodiments, the electrical component 34 can be reversibly coupled to, supported by, or otherwise engaged with the medical device 32 when housed in the cavity 50 (e.g., via snaps, hooks, springs, and/or other internal mechanisms within the cavity 50). The electrical component 34 can thus be at least partially removed or otherwise separated from the medical device 32, for example, permitting an opportunity to clean and sterilize the medical device 32 (e.g., via chemical, heat, or pressure sterilization).

For example, before conducting a medical procedure, the electrical component 34 can be coupled to the medical device 32 (e.g., by opening the handle 38 and inserting the electrical component 34 into the cavity 50). After completion of the procedure, the first member 44 can be separated from the second member 46, the electrical component 34 can be extracted from the cavity 50 for safe storage and/or recharging (as further described below), and the medical device 32 can be cleaned and/or sanitized. Once the medical device 32 is cleaned and/or sanitized, the electrical component 34 can be reinserted into the cavity 50. In this manner, the system 30 can be completely reusable and, in some embodiments, the components (e.g., the electrical component 34, the medical device 32, and/or the display device 36) can be interchangeable with other components.

In other embodiments, the electrical component 34 can be generally, substantially, or completely irremovable with respect to the medical device 32. In other words, the electrical component 34 can be permanently coupled to the medical device 32. For example, the electrical component 34 can be permanently coupled to the handle 38 within the cavity 50 (e.g., permanently coupled to the first member 44 within the first member cavity 52 and/or permanently coupled to the second member 46 within the second member cavity 54). In this example, the members 44, 46 can be coupled together to substantially seal the cavity 50 (e.g., provide an air-tight seal) to protect the internal electrical component 34. In another example, the handle 38 can be a one-piece housing formed around the electrical component 34 (e.g., a one-piece member with a sealed internal cavity that houses the electrical component 34). In such embodiments, the electrical component 34 can be protected when the medical device 32 is cleaned and sterilized (for example, via the seal), thus making the system 30 reusable, and/or the medical device 32 or portions thereof can be substantially disposable (e.g., for one-time use).

FIGS. 6A-8 illustrate another handle configuration, according to some embodiments. As shown in FIGS. 6A-8, the handle 38 can be substantially egg-shaped or generally ellipsoidal-shaped to provide a comfortable feel for the user. In other embodiments, however, the handle 38 can comprise any shape and configuration desired by the user. Furthermore, the handle 38 can include a housing 56 and a support member 58 configured to be received by the housing 56. More specifically, the housing 56 can define an internal cavity 60 with an opening 62 sized and arranged to substantially completely receive the support member 58. As shown in FIGS. 6B and 7B, in some embodiments, the internal cavity 60 can extend substantially an entire length of the housing 56. However, in other embodiments, the internal cavity 60 can span less than the entire length of the housing 56. Additionally, in some embodiments, the opening 62 can be positioned substantially opposite from an aperture (not shown) configured to receive the shaft 40 or other component of the medical device 32.

Generally, the support member 58 can be at least partially removably disposed within the internal cavity 60. In some embodiments, the internal cavity 60 and the support member 58 can be respectively configured and arranged so that the support member 58 can be movably positioned within the internal cavity 60 (e.g., between an "open" position, where the support member 58 extends outside of the internal cavity 60, as shown in FIGS. 6A-8, and a "closed" position, where the support member 58 is completely received within the internal cavity 60). For example, the support member 58 and the internal cavity 60 can be configured so that the support member 58 can slidably ingress and egress from the internal cavity 60 via the opening 62. Also, in some embodiments, walls of the internal cavity 60 can include structures (not shown) configured to guide and retain the support member 58 within the internal cavity 60.

Additionally, in some embodiments, the housing 56 and the support member 58 can comprise features that aid in moving the support member 58 relative to the housing 56 (e.g., between the open and closed positions). For example, in some embodiments, as shown in FIGS. 6A-6B, 7B-7C, and 8, the housing 56 can define a handle notch 64 and/or the support member 58 can define a support notch 66. During ingress and egress of the support member 58 within the internal cavity 60, the housing 56 and support notches 64, 66 can be employed by the user to grasp and/or gain traction in moving the support member 58. In some aspects, a separate tool (not shown) can be used to engage one or both of the housing 56 and support notches 64, 66. In other aspects, the user can employ a body part (e.g., a finger or finger nail) to engage one or both of the housing 56 and support notches 64, 66 to move the support member 58.

Figure 6A:
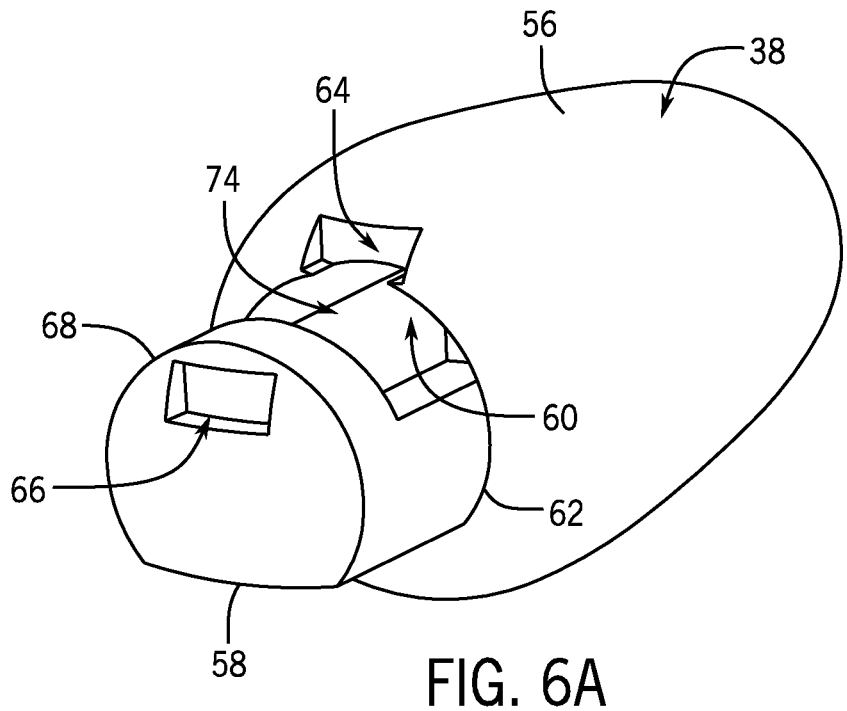
FIG. 6A is a perspective view of a handle of a medical device of some embodiments of the system of FIG. 2.
Figure 6B:
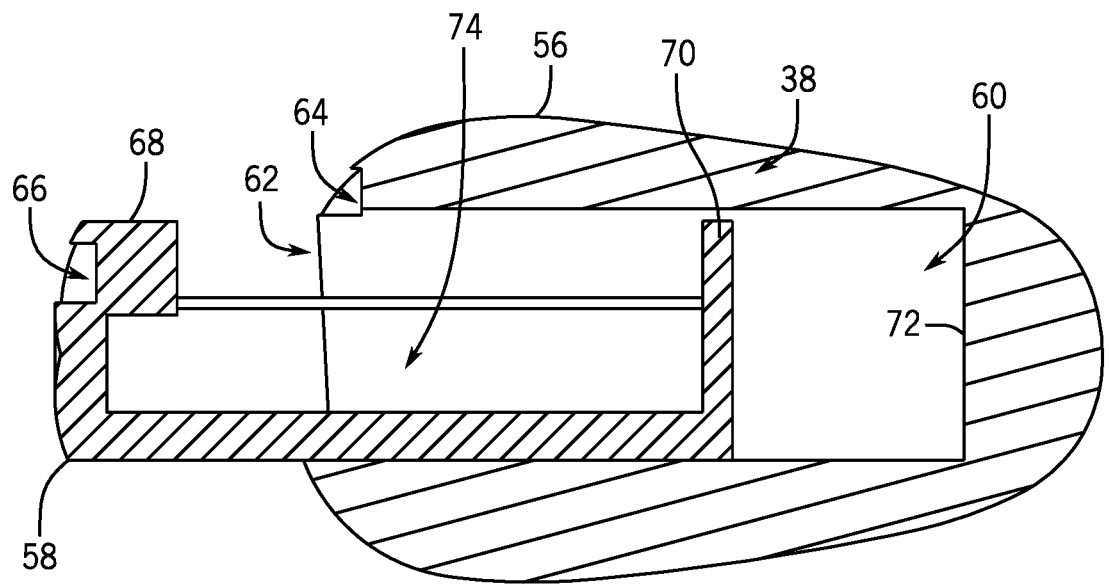
FIG. 6B is a cross-sectional side view of the handle of FIG. 6A.

When received within the internal cavity 60, the support member 58 can substantially seal the internal cavity 60 from outside elements. For example, generally, when received within the internal cavity 60, an outer stop 68 of the support member 58 can close the opening 62, thus sealing the internal cavity 60. Furthermore, in some embodiments, the support member 58 can include an inner stop 70 and the outer stop 68 positioned on opposite ends of the support member 58. When in the closed position, the inner stop 70 can be positioned furthest within the internal cavity 60 (e.g., abutting an internal wall 72 of the internal cavity 60, as shown in FIG. 6B). Conversely, the outer stop 68 can be positioned on the opposite end of the support member 58 as the inner stop 70 (e.g., at the opening 62). As such, when the support member 58 is positioned within the internal cavity 60, the outer stop 68 can partially, substantially, or completely seal the internal cavity 60 and substantially form a portion of an outer wall of the handle 38 (e.g., form part of a surface to be engaged by the user, like the surface 47 described above with respect to FIGS. 4A-4B). Additionally, in some embodiments, the handle 38 can further include a component (not shown) configured to maintain or lock the support member 58 in the closed position within the internal cavity 60.

Figure 7A:
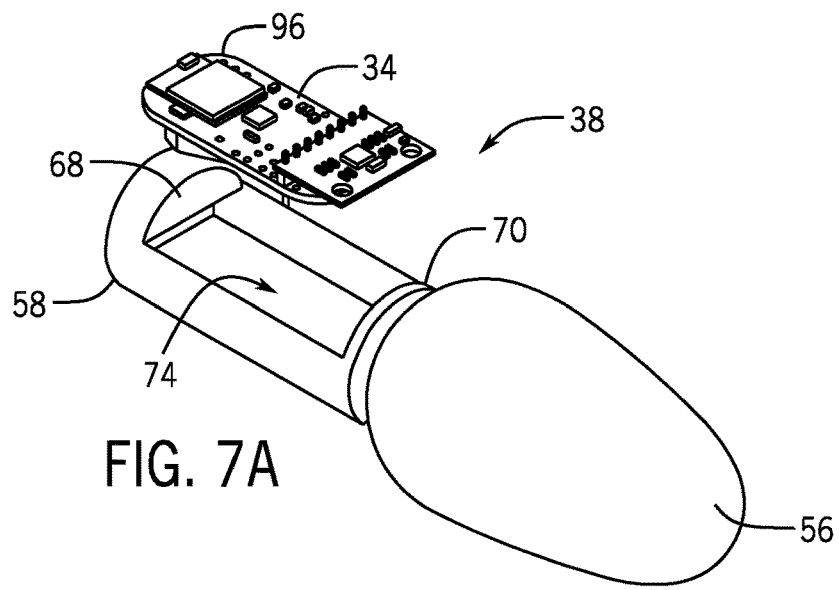
FIG. 7A is an exploded perspective view of the handle of FIG. 6A and an electrical component of some embodiments of the system.
Figure 7B:
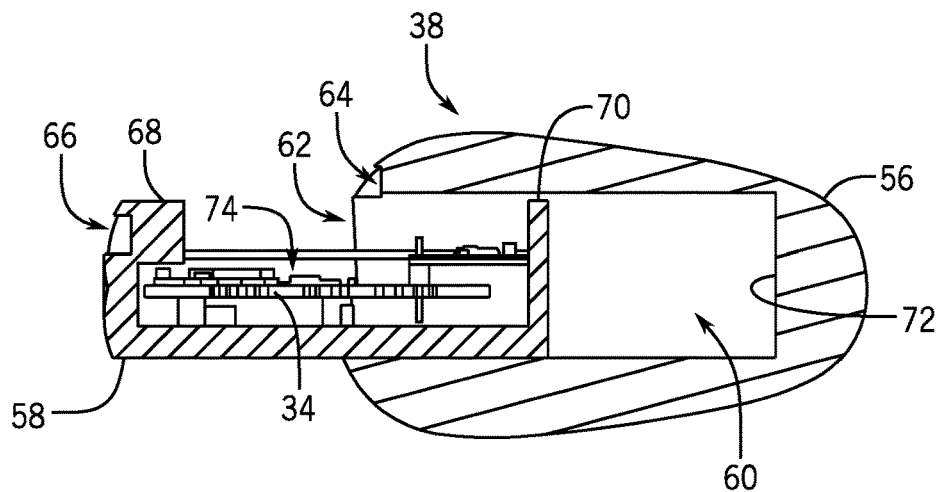
FIG. 7B is a cross-sectional side view of the handle and the electrical component of FIG. 7A.
Figure 7C:
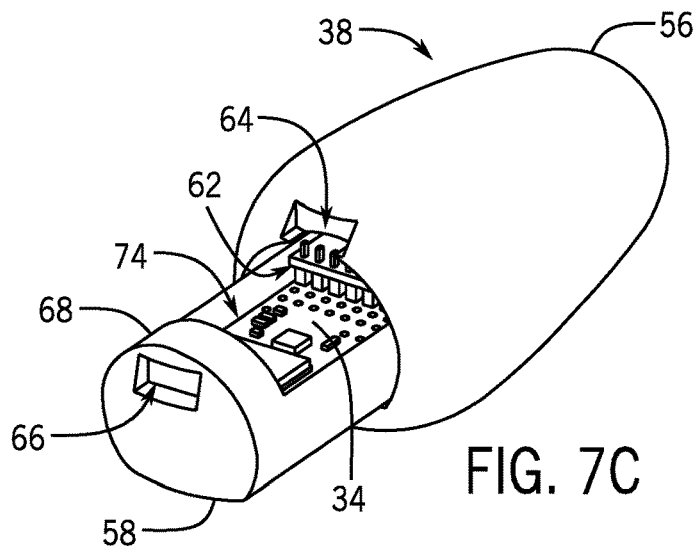
FIG. 7C is a perspective view of the handle and the electrical component of FIG. 7A.
Figure 8:
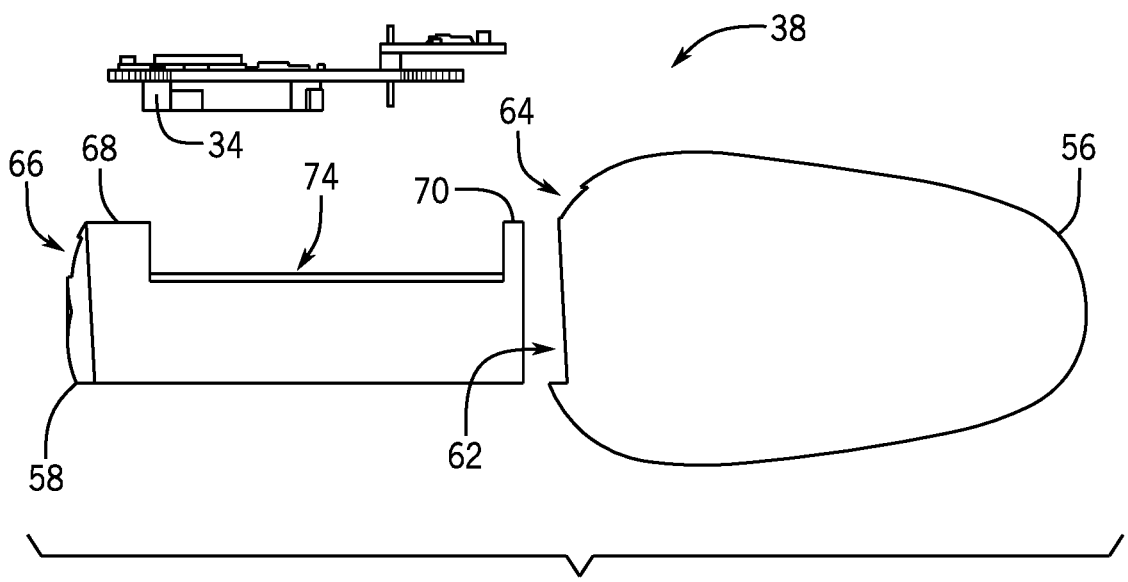
FIG. 8 is an exploded side view of the handle and the electrical component of FIG. 7A.

Additionally, the support member 58 can be configured and arranged to receive some or all of the electrical component 34. More specifically, in some embodiments, the support member 58 can comprise structures that can aid in receiving the electrical component 34. As shown in FIGS. 6A-8, the inner stop 70 and the outer stop 68 can be spaced a distance apart and configured to define a receptacle 74 between the stops 68, 70. As shown in FIGS. 7A-8, the receptacle 74 can be sized to receive and hold the electrical component 34, for example, so that the electrical component 34 is supported and protected from outside elements during a procedure. In addition, the support member 58, including the inner and outer stops 68, 70, can be configured so that the electrical component 34 can be removably positioned within the receptacle 74.

Accordingly, prior to a procedure, the support member 58 can be slid out of the internal cavity 60, e.g., using the notches 64, 66 for assistance, and the electrical component 34 can be positioned or fixed within the receptacle 74. The support member 58 can then be slid back into the internal cavity 60 to substantially seal the internal cavity 60, and the internal electrical component 34, from outside elements during the procedure. Once the procedure is complete, the support member 58 can again be slid out of the internal cavity 60 and the electrical component 34 can be removed from the receptacle 74 to permit cleaning and sterilization of the handle 38 and charging and/or storage of the electrical component 34.

Thus, as described above, the electrical component 34 may be coupled to or otherwise received within the handle. Furthermore, as described above, the handle 38 can be coupled to the shaft 40 to provide a pedicle finder. Moreover, in some embodiments, the handle 38 can be configured to be coupled to other components besides the shaft 40. In other words, in some embodiments, some aspects of the medical device 32, such as the shaft 40, can be capable of being replaced with other functional members, such as a screwdriver, a needle, a curette, a probe, a drill, or other components, to imbue the medical device 32 with other functionalities. In this manner, the medical device 32 can be convertible between different types of devices. By way of example, in some implementations, the medical device 32 can initially be configured as a pedicle finder, including the shaft 40 coupled to the handle 38. After the pedicle finder is no longer needed, the shaft 40 can be removed from the handle 38 and replaced with a different functional element, such as a screwdriver. In this example, the medical device 32 can be configured as both a pedicle finder and a pedicle screwdriver, with a common handle 38 comprising the electrical component 34. Additionally, in some embodiments, the handle 38 can be configured to receive or be coupled to any other component required for an osteotomy or other medically relevant procedure. In any of these configurations, the common handle 38, including the electrical component 34, remains for different forms of the medical device 32. In other words, the handle 38 and the electrical component 34 can be reusable and interchangeable with different components to enable different uses of the medical device 32.

Figure 9:
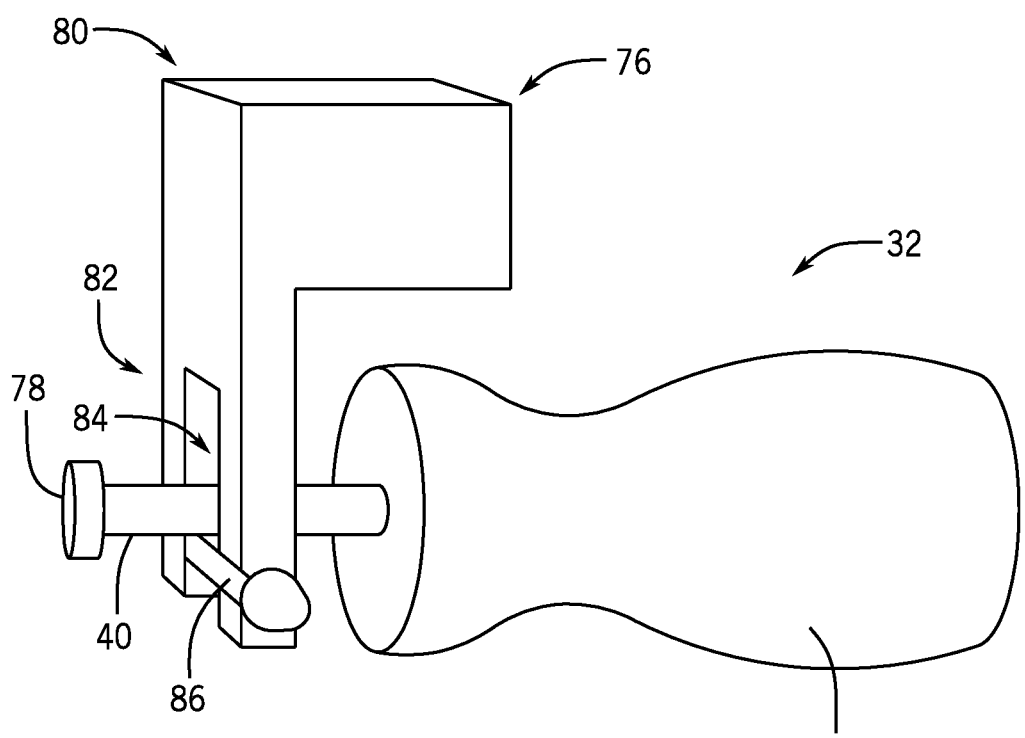
FIG. 9 is a perspective view of a medical device of some embodiments of the system of FIG. 2.
Figure 10:
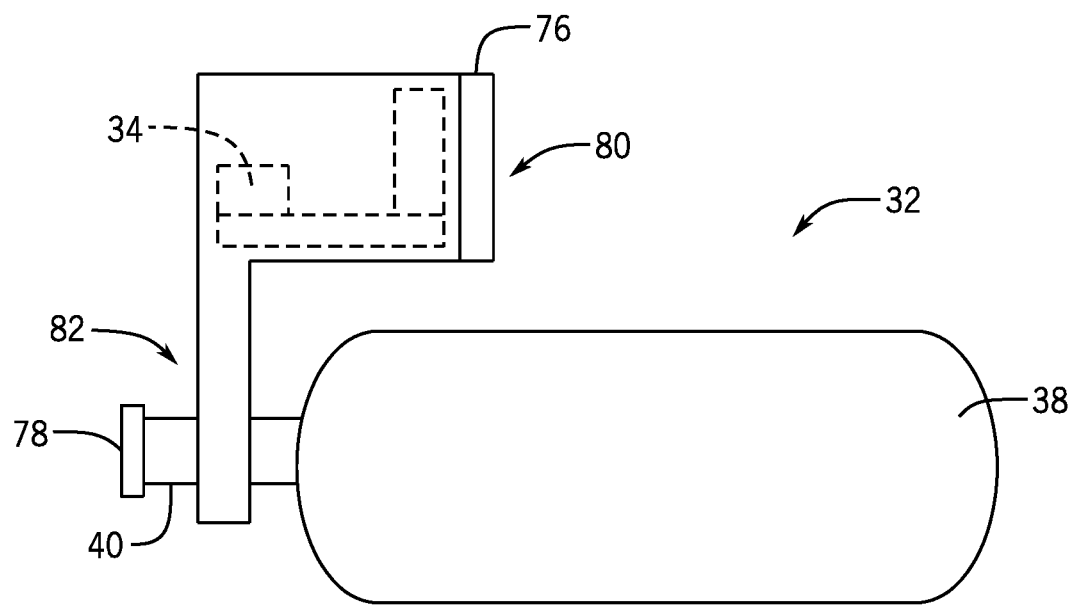
FIG. 10 is a side cutaway view of the medical device of FIG. 9.
Figure 11:
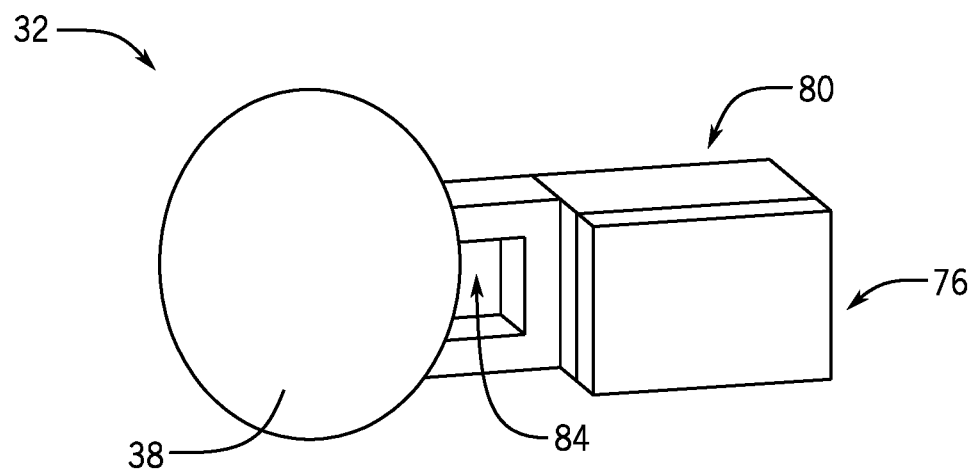
FIG. 11 is a rear view of the medical device of FIG. 9.

FIGS. 9-11 illustrate an alternative medical device configuration, according to some embodiments. As shown in FIGS. 9-11, the medical device 32 can include a handle 38 and a shaft 40, as described above, as well as an additional housing 76 configured to house the electrical component 34. The electrical component 34 can be disposed within the housing 76, as shown in FIG. 10, and the housing 76 can be releasably or permanently coupled to the shaft 40 or the handle 38. For example, in some embodiments, the housing 76 can be configured to be coupled to the shaft 40 adjacent to the handle 38 so that the housing 76 does not impede use of the medical device 32 during a medical procedure. In other words, the housing 76 can be configured to be coupled to the shaft 40 closer to the handle 38 than a tip 78 of the shaft. Furthermore, the housing 76 can be coupled to the shaft 40 in a suitable manner so that the electrical components 34 housed within the housing 76 can measure the orientation or position of the medical device 32, as further described below.

In some embodiments, as shown in FIGS. 9-11, the housing 76 can be configured as an L-frame support member with a receptacle portion 80 and a coupling portion 82. The coupling portion 82 can be reversibly coupled to the shaft 40, and the receptacle portion 80 can be sized and configured to permanently or temporality house the electrical component 34. For example, the coupling portion 82 can include a notch 84 and a lever 86 (as shown in FIG. 9). The lever 86 can be rotatable between an open position that provides access into the notch 84, and a closed position that encloses the notch 84. In this manner, the shaft 40 can be positioned within the notch 84, and the lever 86 can be closed to substantially fix the shaft 40 within the notch 84 and, thus, couple the housing 76 to the shaft 40, as shown in FIGS. 9-11.

Alternatively, in some embodiments, the housing 76 can be coupled directly to the handle 38 or other components of the medical device 32. Furthermore, in some embodiments, the electrical component 34, by itself, can be reversibly or permanently coupled to any portion of the medical device 32. Moreover, in yet other embodiments, the electrical component 34 can comprise an attachment mechanism (not shown) configured to directly couple the electrical component 34 to the medical device 32 (e.g., to an outside of the handle 38 or the shaft 40). By way of example, an attachment mechanism can comprise a flexible band that can be reversibly disposed on the handle 38 or shaft 40 of the medical device 32. In another example, the electrical component 34 can include an attachment mechanism in the form of a plug-in type connector (not shown) configured to be received within a receptacle on the handle 38 or the shaft 40.

Additionally, in any of the above-described embodiments of FIGS. 3A-11, the medical device 32 can include additional components. For example, in some embodiments, the medical device 32 can include one or more illumination devices, such as light-emitting diodes (not shown), to provide additional illumination during a procedure. In some embodiments, at least a portion of the one or more illumination devices can be configured as a laser or light-emitting diode configured to provide illumination and/or to provide targeting or guidance information to a user. For example, in one embodiment, the illumination device can be positioned on the handle 38 and activated to illuminate the shaft 40 and/or to illuminate an area surrounding the tip 78 of the shaft 40 in order to provide illumination and/or targeting or guidance information to the user.

Referring now to the electrical component 34, FIG. 12 schematically illustrates the electrical component 34, according to some embodiments. Generally, as shown in FIG. 12, the electrical component 34 can comprise a plurality of constituents including, but not limited to, an inertial measuring unit 88, a controller 90, a power source 92, and/or a current unit 94. In some embodiments, as shown in FIGS. 3B, 5A-5B, 7A-7C, and 8A, the constituents can be housed on one or more control boards 96. In one embodiment, all constituents of the electrical component 34 can be housed on or be part of a single control board 96, thus permitting easy insertion and removal of the electrical component 34 from the handle 38 or the housing 76. Additionally, while the constituents are illustrated and described herein as separate components, some embodiments may include a single component having functionality of one or more constituents. Furthermore, while the electrical component 34 is referred to and described herein as a single element, the electrical component 34 may instead comprise a plurality of electrical components 34 in some embodiments.

In some embodiments, the inertial measuring unit 88 can include one or more sensors and can be used to measure or detect movement and/or a relative position or angle of the electrical component 34 and, by extension, the medical device 32 (e.g., because the electrical component 34 is housed within or coupled to the medical device 32). As such, the inertial measuring unit 88 can generate data regarding the orientation, angle, and/or position of the medical device 32, for example, to be processed elsewhere (such as the by the controller 90 or by one or more processors of the display device 36).

According to some embodiments, the inertial measuring unit 88 can comprise one or more of a gyroscope and an accelerometer, for example, to detect or measure angle or position information along two or three axes. For example, the gyroscope can measure and/or help maintain an orientation of the electrical component 34 and the medical device 32. Furthermore, the accelerometer can be used to measure acceleration of the electrical component 34 and the medical device 32. Together, these subunits of the inertial measuring unit 88 can detect or assess orientation of the medical device 32 (e.g., when the electrical component 34 is coupled to the device 32) along two or three axes. More specifically, these subunits can detect or assess an orientation of the medical device 32 relative to a calibrated position, for example, using the direction of gravity for reference, and where the medical device 32 moves from the calibrated position.

Accordingly, in some embodiments, the inertial measuring unit 88 can be used to measure or detect a medial angle and/or a sagittal angle of the medical device 32 relative to the calibrated position. For example, in some embodiments, the inertial measuring unit 88 can include a measurement range between about 0 degrees and about 180 degrees, between about 0 degrees and about 80 degrees, or between about 0 degrees and about 40 degrees in the sagittal and/or the transverse planes. Additionally, in some embodiments, the inertial measuring unit 88 can comprise components in addition to or in lieu of the gyroscope and/or the accelerometer. For example, the inertial measuring unit 88 can comprise any suitable sensor(s) or component(s) capable of measuring inertia and/or other movement of the electrical component 34 and the medical device 32. In one example, the inertial measurement unit 88 can further include a magnetometer.

Furthermore, in some embodiments, the electrical component 34 can be configured and arranged to measure movement of the medical device 32 in addition to or in lieu of the above-described angle data. For example, the inertial measuring unit 88 (or another component of the electrical component 34) can be configured to measure displacement, such as linear and/or translational displacement of the medical device 32. For example, to accomplish this functionality, the inertial measuring unit 88 can use the accelerometer, which can measure orientation and position, and the gyroscope, which can measure orientation, and use such measurements with a mathematical formula to calculate displacement from a zero reference point. In another example, other displacement sensors may be used, such as, but not limited to, capacitive sensors, eddy current sensors, or magnetic field sensors. Alternatively or additionally, to accomplish this functionality, an optical tracking system (e.g., including one or more cameras, such as infra-red cameras, to track one or more light emitting diodes) or a magnetic tracking system may be incorporated into the device 32. Using any of these configurations, the electrical component 34 can measure a depth of portions of the medical device 32. By way of example, the electrical component 34 in such embodiments can be configured and arranged to measure depth of insertion of portions of the device 32, such as the shaft 40, during a medical procedure. In certain embodiments in which the medical device 32 is configured as a pedicle finder, the electrical component 34 can provide the user with valuable information regarding depth and/or distance that the shaft 40 has penetrated the pedicle to aid the user in guiding the shaft 40 and minimizing a risk that the user over-inserts the shaft 40 and perforates the pedicle.

In some embodiments, the electrical component 34 can also comprise a power source 92. The power source 92 can be integral with or otherwise connected to the electrical component 34 so that the power source 92 can provide current to drive operation of the various constituents of the electrical component 34. For example, the power source 92 can be a disposable or re-chargeable battery (e.g., alkaline battery, lithium-ion battery, dry-cell battery, etc.). In some embodiments, as described above, the electrical component 34 can be removed from the medical device 32 after a medical procedure to permit recharging of the power source 92 and/or sterilization or cleaning of the medical device 32.

Additionally, in some embodiments, the electrical component 34 can include a current unit 94 configured and arranged to generate a current. More specifically, in some embodiments, at least a portion of the medical device 32, such as the shaft 40, can include electrically conductive material. Furthermore, the electrical component 34 can be coupled to or arranged within the medical device 32 to be in communication with this conductive portion. In this manner, the current unit 94 can generate a current (e.g., via the power source 92) to flow from the electrical component 34 through the conductive portion. For example, during certain medical procedures in which the medical device 32 is positioned adjacent to the spine, such as a spinal fusion, the current unit 94 can be used provide guidance information to a user. More specifically, in order to ensure that the medical device 32 has not inappropriately breached any structure and has contacted the spine during guide-hole creation, an electrical current (such as around 20 milliamperes) can be circulated through the medical device 32 via the current unit 94. If the conductive portion of the medical device 32 (such as the shaft 40) has contacted the spine, a circuit will be completed and the subject will involuntarily move when a grounding wire is affixed to the subject. Accordingly, the current flowing from the electrical component 34 through the medical device 32 can provide key guidance information for the user during positioning of guide holes.

In some embodiments, the electrical component 34 can comprise the controller 90. The controller 90, which can be a microcontroller, can be configured to aid in controlling one or more functions of the electrical component 34 and its constituents. In one embodiment, the microcontroller 90 can comprise a Bluetooth microcontroller, such as LightBlue Bean Bluetooth controller. In other embodiments, the electrical component 34 can comprise other forms and types of microcontrollers and/or other forms of technologies capable of operating the electrical component 34. For example, the microcontroller 90 can power and control the inertial measuring unit 88, receive data from the inertial measuring unit 88, process the data, establish a connection with the display device 36, communicate the raw data and/or processed data to the display device 36 (e.g., via a Bluetooth connection), receive information or instructions from the display device 36, operate the current unit 94, provide current unit functionality, and/or operate an illumination device of the medical device 32. For example, in some embodiments, the microcontroller 90 can incorporate data fusion algorithms and/or data communication routines configured to process and communicate measurement data to the display device 36. In another example, in some embodiments, the microcontroller 90 can sense a connection to the medical device 32 so that, when not connected to the medical device 32, the microcontroller 90 places the electrical component 34 in a sleep or low power mode to conserve battery life of the power source 92. Furthermore, other functionalities of the microcontroller 90 can be contemplated within the scope of certain embodiments of the invention.

As noted above, the system 30 can further comprise the display device 36. Generally, in some embodiments, the display device 36 can wirelessly connect to the electrical component 34, communicate with the electrical component 34 to receive data and/or transmit instructions, process data from the electrical component 34, display information to a user, receive instructions and/or other inputs from the user, and/or store data in memory. For example, in some embodiments, the display device 36 can include one or more processors operating under the control of one or more computer programs or applications loaded from a non-transitory computer-readable memory to accomplish one or more of the above functions. The processor(s) can execute the programs or applications to implement method steps of some embodiments. Accordingly, as described herein, reference to a step or process performed via a computer program is also a reference to the processor that performed that step. In some embodiments, the display device 36 can comprise at least one of a tablet, a personal digital assistant, a smart phone, a smart watch, a laptop computer, a desktop computer, a monitor, a smart television, an MP3 player (e.g., an iPod®) or any other technology that can be used to view DICOM images. In one embodiment, the display device 36 can include a dedicated application (such as an iOS app) for use with the medical device 32 and the electrical component 34.

Figure 3C:
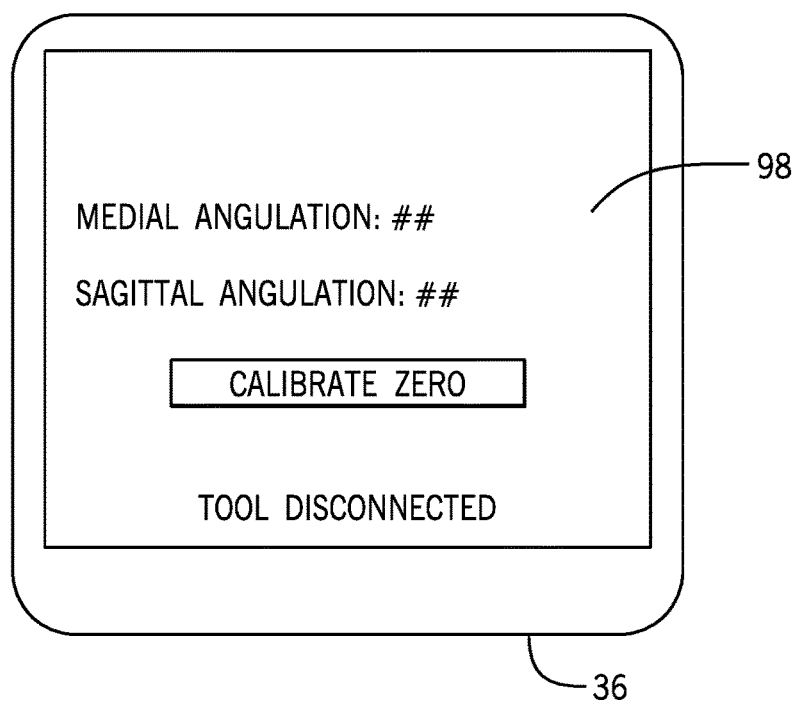
FIG. 3C is an illustrative front view of a display device, displaying angular data for a user, of some embodiments of the system of FIG. 2.

As shown in FIGS. 2, 3C, and 12, the display device 36 can be in communication with the electrical component 34 and, by extension, the medical device 32 (i.e., when the electrical component 34 is coupled to or received within the medical device 32). In some embodiments, the electrical component 34 and the display device 36 can be in constant or substantially constant communication in order to provide real-time or near-real time guidance information to a user during a medical procedure.

In some embodiments, the display device 36 can be in substantial or complete wireless communication with the electrical component 34. As such, the display device 36 and the medical device 32 may be physically separate from each other. For example, in such embodiments, the display device 36 and the electrical component 34 can communicate via the Bluetooth microcontroller 90 of the electrical component 34. Accordingly, the display device 36 can be configured to receive a Bluetooth signal and the microcontroller 90 can be capable of a strong enough signal strength to communicate with the display device 36, for example, despite a noisy operating environment. In other aspects, the display device 36 can wirelessly communicate with the electrical component 34 using any other conventional wireless communication protocol. In other embodiments, the electrical component 34 or the medical device 32 can be coupled to the display device 36 to enable wired communication. In such embodiments, a structure such as a USB cable, a mini-USB cable, a micro-USB cable, an HDMI cable, or any other structure capable of transmitting data from the electrical component 34 to the display device 36 can be used.

Generally, the display device 36 can display information to guide a user in positioning the medical device 32 during a medical procedure. In some embodiments, as shown in FIGS. 3C and 12, the display device 36 can include a graphical user interface 98. For example, data transmitted from the electrical component 34 can be processed by the display device 36 and then the resulting processed data can be displayed to the user via the graphical user interface 98. More specifically, in some embodiments, a processor of the display device 36 can use the data received from the electrical component 34 (e.g., the inertial measuring unit 88) to assess orientation, angulation, position, and/or the changes in the physical location of the medical device 32.

From this assessment, the processor (or another processor) can control the graphical user interface 98 to display the orientation, angle, position, and/or location information to the user.

For example, as described above, the electrical component 34 can detect medial angle and or sagittal angle of the medical device 32 relative to a calibrated reference position. As shown in FIG. 3C, the display device 36, via the graphical user interface 98, can display information related to the detected medial angle and/or sagittal angle. In other embodiments, the graphical user interface 98 can display other data, such as a grid to provide the user with relative orientation information. Furthermore, in some embodiments, the graphical user interface 98 can be configured to display instructions to the user during a medical procedure. For example, the graphical user interface 98 can display an instruction for the user to align the medical device 32 for calibration.

Additionally, the display device 36 can be configured to provide additional data to the user, such as fluoroscopic images, computed tomography (CT) images, radiographic images, and outputs from other imaging modalities. For example, in some conventional procedures, medical professionals rely, at least in part, on radiation-based imaging modalities to guide placement of the spinal fusion apparatus throughout the procedure. As a result, the surgeon, patient, and others present for the procedure may be exposed to radiation. Over the course of a surgeon's career, this additional radiation can accumulate, putting the surgeon at significant health risks. In some embodiments, the system 30 and display device 36 can be used in conjunction with these conventional imaging outputs in order to reduce the need for additional radiation-based procedures throughout the medical procedure. More specifically, the display device 36, can display angulation information as well as images of the subject, including fluoroscopic images, CT images, and/or outputs from other imaging technologies so that the user has an extensive amount of data regarding positioning of the medical device 32. The real-time or near real-time angulation data from the system 30 can reduce the need for extensive and ongoing radiation-based imaging techniques during the surgical procedure.

Moreover, in some embodiments, the display device 36 (e.g., through a computer program executed by a processor) can manipulate the angulation data and the various imaging files to display imaging overlays for the user so that the various forms of data displayed on the graphical user interface 98 are integrated to provide significant additional guidance to the user. In some embodiments, the display device 36 can also process the angulation data to overlay a trajectory on the images, thus providing further guidance to the user. Alternatively, the display device 36 can display the above-described information in a side-by-side manner or in an alternating manner. Furthermore, in some embodiments, the display device 36 can display a stored target or desired angle or orientation (e.g., concurrently with the measured angles, position, orientation, and/or location). Additionally, in some embodiments, the display device 36 can provide instructions to the user to orient or position the device to reach a desired or target angle, orientation, or position. Accordingly, the display device 36 may be substantially passive (e.g., displaying information to the user) in some embodiments, and/or active (e.g., providing instructions to the user) in some embodiments.

Furthermore, a user can interact with the system 30 through the graphical user interface 98. For example, in some embodiments, the display device 36 can be configured as a device with a touch screen through which the user can interact with the system 30. For example, as shown in FIG. 3C, the graphical user interface 98 can display one or more icons that can enable the user to calibrate the angulation measure of the system 30 (e.g., by selecting a desired icon via the touch screen). In some embodiments, the display device 36 can comprise other configurations so that additional inputs (e.g., a computer mouse, buttons or other input elements) can be used to interact with the system 30. Additionally, in some embodiments, a user can provide user inputs (e.g., by interacting with the graphical user interface 98 and/or using other input elements), for example, to activate or deactivate the system 30, turn on an illumination device, activate the electrical current unit, provide a desired or target angulation, position, or orientation, indicate a component currently coupled to the handle 38 (e.g., a shaft, a screwdriver, a needle, a curette, a probe, a drill, or another component), and/or provide other instructions to the system 30.

FIG. 13A illustrates an example operation method of some embodiments of the system 30. Generally, operations of the system 30 can vary depending on implementations preferred or desired by the user and, as described below, can include sub-operations. The following exemplary methods are described in context of a spinal fusion procedure (e.g., with a medical device 32 configured as a pedicle finder), but these examples are intended to be non-limiting in that the methods may be adapted for any medical device configuration and related medical procedure.

Generally, as shown in FIG. 13A, a method of providing angular or position guidance during a medical procedure can include an initial step of turning on or activating the system 30 (step 100). After step 100, the method can include calibrating the medical device 32 (step 200), inserting the medical device 32 into a portion of the subject (step 300), and then checking the orientation of the device (step 400). As shown in FIG. 13A, steps 300 and 400 can be repeated and/or performed simultaneously. Thereafter, the medical device 32 can be removed from contact with the subject (step 500) and steps 200, 300, 400, and 500 can be repeated for each pedicle screw (and, more specifically, each guide hole) that may be necessary to complete the medical procedure. Finally, the system 30 is turned off or deactivated (step 700).

More specifically, step 100 can include activating the electrical component 34. Activating the electrical component 34 can be accomplished by, for example, a user providing an input instruction via the graphical user interface or another user interface, the user inserting or connecting the power supply, and/or the display device 36 activating a computer program or application stored in memory that automatically activates the electrical component 34. In some embodiments, activated can mean powering on the electrical component 34 or waking up the electrical component 34 from a sleep mode or low-power mode. Additionally, in some embodiments, activation can be accomplished by the user opening the handle 38 (e.g., uncoupling the members 44, 46 or sliding out the support member 58 from the housing 56) and positioning the electrical component 34 within the handle 38.

At step 200, the medical device 32 is calibrated. More specifically, as shown in FIG. 13B, step 200 can include multiple sub-steps intended to zero-out and/or calibrate the orientation or position of the medical device 32 (e.g., via the electrical component 34 coupled to and/or disposed within the medical device 32). In some embodiments, the calibration step 200 can include initially aligning the medical device 32 with gravity (step 210), then receiving user input to calibrate the current alignment (step 220). For example, at step 220, the display device 36 can display, via the graphical user interface 98, a "Calibrate Zero" icon for the user to press or select, as shown in FIG. 3C. At step 230, the user can further set a desired target orientation and/or target angle by selecting options displayed on the graphical user interface 98. For example, the desired target orientation or angle can be determined preoperatively by the user, for example, using anatomical charts or calculations based on preoperative imaging of the subject. After receiving the user inputs, a processor of the display device 36 can store the desired target orientation, for example, in the memory of the display device 36 or external memory (step 240). Once the storage step 240 is complete, the method can proceed to steps 300 and 400.

At step 300, the medical device 32 is inserted into the subject and, at step 400, medical device orientation is observed. More specifically, as shown in FIG. 13C, sub-steps of steps 300 and 400 can be executed concurrently. For example, when inserting the medical device 32 into the subject (step 300), the user can initially insert a tip 78 of the medical device 32 into a vertebra of the subject (step 310), which can be followed by, in a substantially or completely concurrent manner, checking the orientation of the medical device 32 (step 400), the user further driving the medical device 32 through a portion of the vertebra (step 320), and/or monitoring resistance of the bone of the vertebra (step 330). For example, step 330 can be accomplished by feel by the user or by one or more sensors such as, but not limited to, a force sensing device (e.g., a piezoelectric force sensor or a strain gauge) incorporated into the shaft 40 or between the shaft 40 and the handle 38. Additionally, in embodiments that incorporate force sensing and linear displacement capabilities, stiffness may also be determined for whatever tissue the device 32 is in contact with (e.g., by calculating force divided by displacement).

With respect to step 400, checking the orientation of the medical device 32 can include displaying to the user, via the display device 36, a current medial and/or sagittal angle of the medical device 32 (as determined by the electrical component 34) and, optionally, the stored target angles (step 410). If necessary, the user can adjust the medical device 32 to the target desired orientation and/or target angle (step 420). Some or all of the sub-steps of steps 300 and 400 can be implemented in a repeated and/or continuous manner to provide the user with real-time or near real-time feedback regarding insertion and positioning of the medical device 32. After completing steps 320, 330, 400, 410, and/or 420 one or more times, the user can reach a desired or set penetration depth within the vertebra of the subject (step 340). The set depth can be determined by freehand or by feedback guidance through the display device 36.

Once the user has reached a set depth at step 340, the user can remove the medical device 32 from the subject at step 500. The user can repeat steps 200-500 to create guide holes for each pedicle screw that may be necessary to complete the medical procedure (step 600). Upon completion of step 600, the system 30 can be turned off or deactivated at step 700. In some embodiments, step 700 can be accomplished in a similar, but opposite manner as step 100. More specifically, step 700 can include deactivating the electrical component 34, for example, via a user providing an input via the graphical user interface or another user interface, via the user removing or disconnecting the power supply, and/or via the display device 36 activating a computer program or application stored in memory. Additionally, in some embodiments, deactivation can be accomplished by the user opening the handle 38 (e.g., uncoupling the members 44, 46 or sliding out the support member 58 from the housing 56) and remove the electrical component 34 from within the handle 38.

Figure 14:
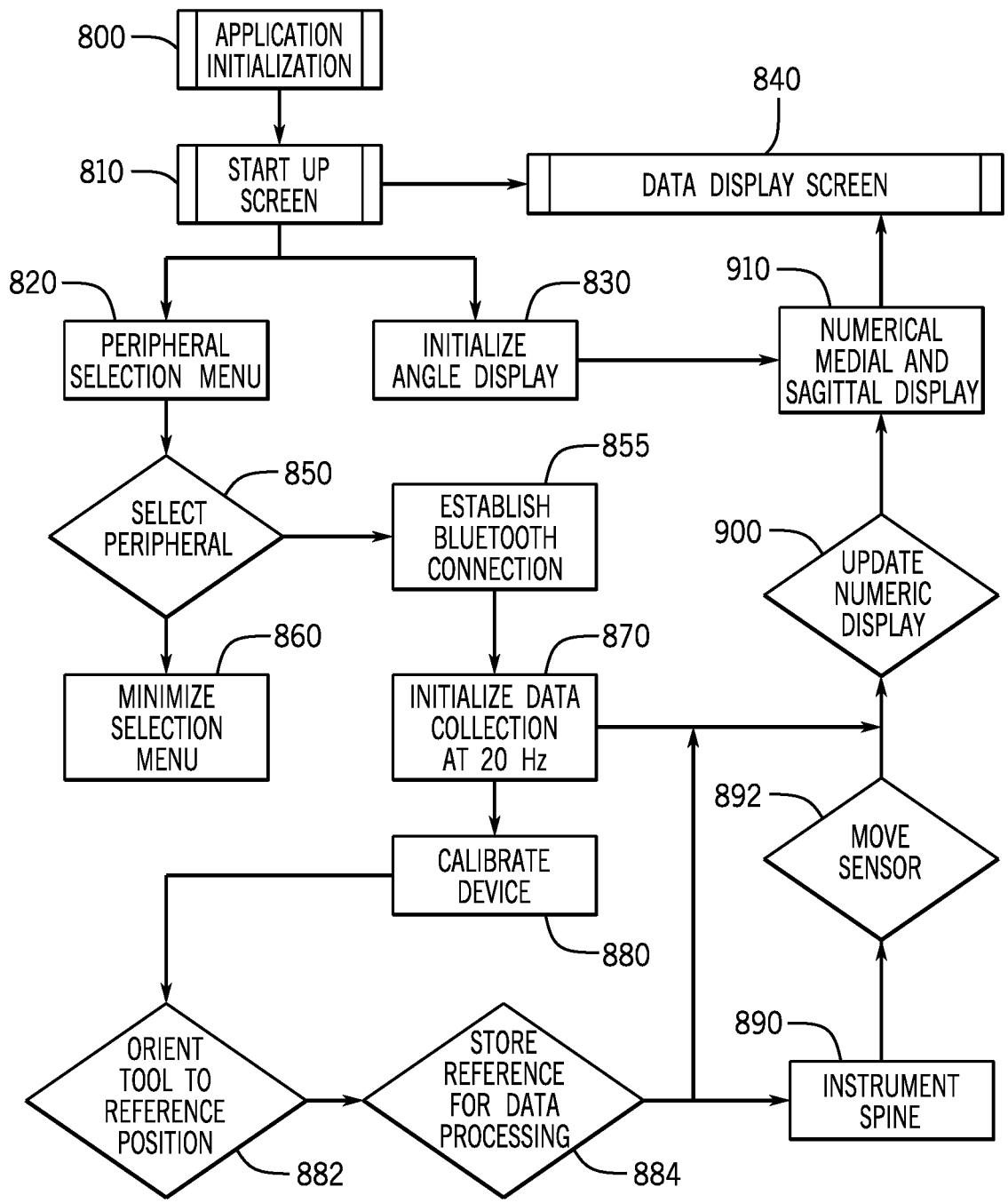
FIG. 14 is a flow diagram of an application method for advanced medical device placement and guidance, according to some embodiments.
Figure 15:
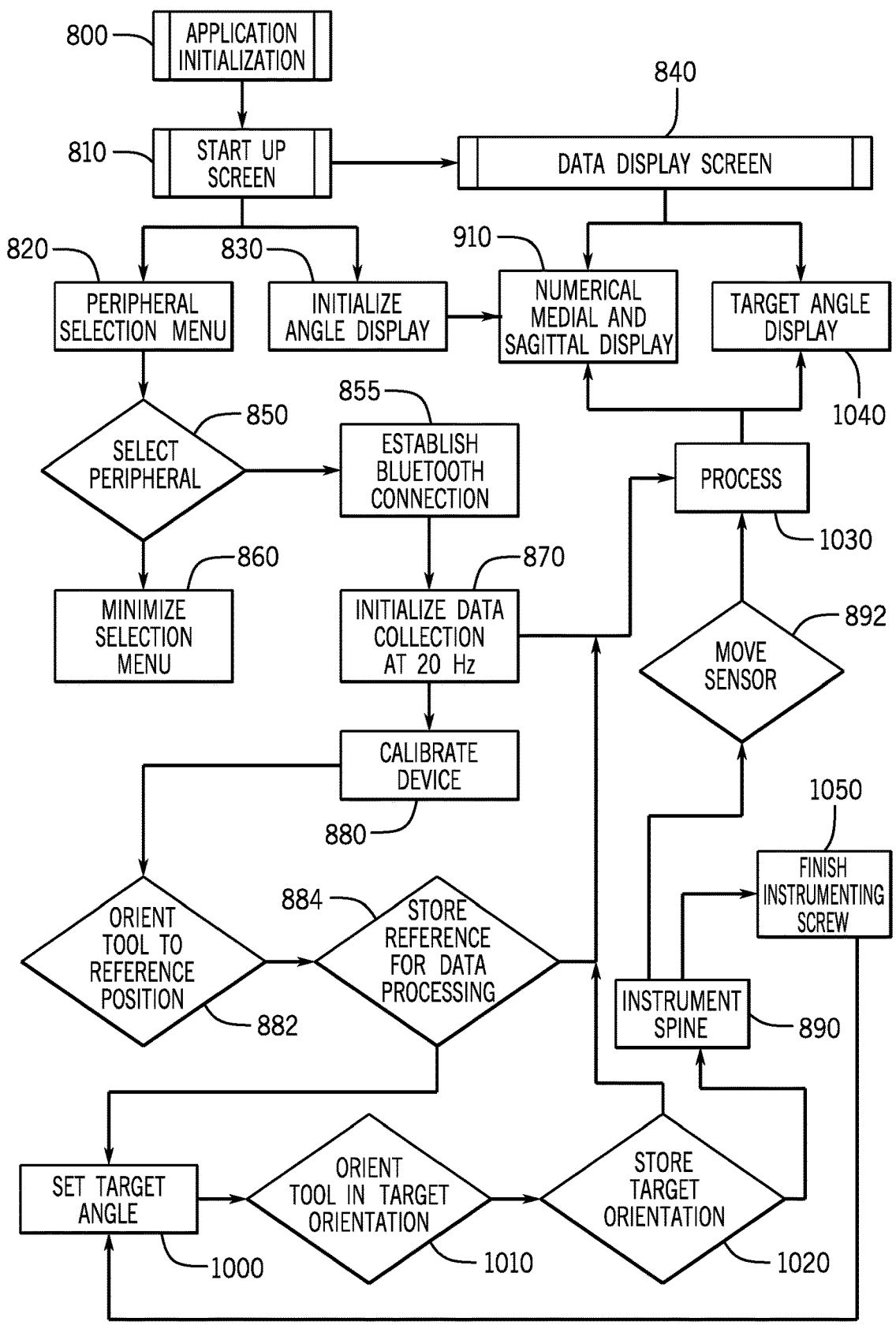
FIG. 15 is another flow diagram of an application method for advanced medical device placement and guidance, according to some embodiments.

As described above, the display device 36 can include one or more processors, memory, and one or more applications or computer programs stored in the memory. In some embodiments, at least one of the applications stored in the memory can comprise instructions for guiding the processor to process data received from the electrical component 34. For example, FIGS. 14 and 15 illustrate application methods, according to some embodiments, that can be executed by the processor. The method steps described herein are intended to be illustrative and non-limiting with respect to operations of the application, processor, and display device 36.

For example, FIG. 14 illustrates a method that can be employed by the system 30 (e.g., as steps of an application carried out by a processor) of some embodiments. The method can begin with an initialization step 800. For example, the method can be initialized at step 800 when a user selects and/or activates an application that is stored in memory of the display device 36 (e.g., by selecting an icon on the graphical user interface 98). After the initialization step 800, at step 810, a start-up screen process can be executed, which can include displaying, via the graphical user interface 98, a peripheral selection menu (step 820). The start-up screen process can also include initializing an angle display (step 830) and executing a data display screen process (step 840), which can further include displaying, via the graphical user interface 98, numerical angle values (step 910), as further described below.

Using the peripheral section menu from step 820, the user can select a peripheral device (at step 850) for communication with the display device 36. For example, the user can select to establish a Bluetooth connection (at step 855) with a peripheral device, such as the medical device 32 and electrical component 34. After the peripheral device has been selected, the peripheral selection menu 820 can be minimized at step 860 and accessed at a later time in the event that the user wishes to select a different medical device 32.

After connection is established with the electrical component 34 (e.g., the peripheral device), data collection can be initialized between the electrical component 34 and the display device 36 at step 870. For example, data collection can occur at a frequency of approximately 20 Hz. In other embodiments, however, data collection can occur at any frequency compatible with surrounding medical equipment. After initiating data collection at step 870, the user can calibrate the device at step 880. In some embodiments, the calibration step 880 can be similar to the calibration step 200 of FIGS. 13A-13B. For example, as illustrated in FIG. 14, the calibration step 880 can include the user orienting the medical device 32 to a reference or calibrated position at step 882 (e.g., aligning with medical device 32 with gravity, vertically aligning the medical device 32, horizontally aligning the medical device 32, or otherwise orienting the medical device 32), and then storing the measured current position, orientation, and/or angle as reference values for data processing at step 884. In other embodiments, the calibration steps 880, 200 can differ to meet user needs.

Once the reference value or values are stored at step 884, the user can begin the medical procedure by instrumenting the spine of the subject at step 890 and, optionally, moving the medical device 32 and electrical component 34 at step 892. During these steps, the inertial measurement unit 88 can generate data regarding, for example, angle, orientation, or position information, and such data can be communicated to the display device 36. The data can be processed by the processor of the display device 36, which can then update the current medial and sagittal angles, at step 900, and output the updated angles at step 910. In some implementations, the displayed medial and sagittal angles can be calculated relative to the stored reference position, orientation, and/or angle described above (i.e., stored in step 884 during the calibration step 880). Accordingly, the updated numeric display in step 900 leads to changes in the medial and sagittal angles displayed on the display device 36 at step 910 (e.g., changes relative to the stored reference position) so that the user can either continue movement at the present angle or change the angle of the medical device 32 (e.g., a pedicle finder) to form a correctly aligned guide hole.

Additionally, FIG. 15 illustrates another method that can be employed by the system 30 (e.g., as steps of an application carried out by a processor) of some embodiments. Generally, FIG. 15 can include similar steps 800-910 as described above with respect to FIG. 14. However, in some embodiments, the functionalities of these steps can be varied to meet user needs.

Furthermore, in the method of FIG. 15, after the calibration step 880, the user can also set a target angle at step 1000. In some embodiments, by permitting the user to select a target angle, the system 30 can provide real-time or near real-time feedback, that is continuously updated, regarding the desired orientation, angle, and/or position of the medical device 32 relative to the actual orientation, angle, and/or position. As such, the user can more accurately instrument the spine at step 890. For example, when selecting the target angle at step 1000, the user can position the medical device 32 in a target orientation or angle at step 1010 and the processor can store this desired target orientation or angle (e.g., medial and/or sagittal angles, as measured by the electrical component 34) at step 1020. Alternatively, in some embodiments, the user can input the target orientation or angles via the graphical user interface 98.

Once the target orientation is stored, while the user is instrumenting the spine at step 890 and moving the medical device 32 at step 892, the processor of the display device 36 can process the position data received from the electrical component 34. More specifically, the processor can process the data to determine the current orientation, position, and/or angle of the medical device 32 and determine whether and how much that orientation, position and/or angle deviates from the target orientation at step 1030. Thereafter, at steps 1040 and 910, the display device 36 can display, via the graphical user interface 98, the actual medial and sagittal angles and the stored target orientation 1040 (e.g., target medial and sagittal angles), respectively. As mentioned above, the user can use this comparative information to guide the positioning and angulation of the medical device 32 during the procedure. Thereafter, at step 1050, once the user is satisfied with the position of the guide hole, the user can remove the device 32 and set a new target angle/orientation at a different vertebra or at a different position on the same vertebra.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A system for providing orientation data to a user during a medical procedure performed on a subject, the system comprising:
    a medical device configured to engage a portion of the subject and including a handle, the handle including a first member and a second member removably coupled together, the first member and the second member defining an internal cavity of the handle when coupled together, wherein the first member comprises a receptacle sized to hold an electrical component and the second member comprises an opening sized to slidably receive the first member;
    the electrical component disposed completely within the internal cavity and configured to generate data related to an orientation of the medical device during the medical procedure, the electrical component further configured to be removed from the internal cavity after the medical procedure; and
    a display device physically separate from the medical device and in communication with the electrical component, the display device including a processor configured to
        receive and process the data related to the orientation of the medical device, and
        display information related to the orientation of the medical device to the user based on the data.

2. The system of claim 1, wherein the medical device comprises one of a pedicle finder and includes a shaft coupled to the handle or a pedicle screwdriver and includes a screwdriver coupled to the handle.

3. The system of claim 1, wherein the electrical component is configured to detect one of a medial angle and a sagittal angle of the medical device relative to a reference position.

4. A pedicle angle finder system to provide guidance to a user during a medical procedure performed on a subject, the system comprising:
    a medical device including a handle and a shaft,
        the handle including a first member and a second member removably coupled together, the first member and the second member defining an internal cavity when coupled together, wherein the first member comprises a receptacle sized to hold an electrical component; and the second member comprises an opening sized to slidably receive the first member,
        the shaft coupled to the handle and configured to engage a pedicle of the subject during the medical procedure;
    the electrical component removably positioned within the internal cavity, the electrical component configured to generate data related to a medial angle and a sagittal angle of the handle during the medical procedure, the electrical component further configured to be removed from the internal cavity after the medical procedure; and
    a display device in wireless communication with the electrical component and including a processor configured to
        receive and process the data from the electrical component, and
        display information related to the medial angle and the sagittal angle of the handle to the user based on the data
    wherein the electrical component is completely disposed within a portion of the medical device.

5. The system of claim 4, wherein the electrical component is supported by the first member within the internal cavity.

6. The system of claim 4, wherein the electrical component includes at least one of an inertial measuring unit with an accelerometer and a gyroscope and a microcontroller.

7. The system of claim 4, wherein the electrical component is removably coupled to the handle.

8. The system of claim 4, wherein the processor of the display device is further configured to display images of the subject obtained by at least one of fluoroscopy and a CT scan concurrently with the information.

9. The system of claim 4, wherein a portion of the medical device is electrically conductive, and the electrical component is configured to generate a current through the electrically conductive portion.

10. The system of claim 4, wherein the medical device comprises an illumination source.

11. The system of claim 4, wherein the handle is substantially egg shaped.

12. A method of providing angular guidance to a user during a medical procedure performed on a subject using a system comprising a medical device, an electrical component, and a display device, the method comprising the steps of:
   a) coupling the electrical component to the medical device, including positioning the electrical component within an internal cavity of a handle of the medical device, the internal cavity defined by a first member and a second member coupled together, and coupling together the first member and the second member so that the electrical component is completely disposed within the internal cavity;
   b) establishing a wireless connection between the electrical component and the display device;
   c) generating data, via the electrical component, related to a medial angle and a sagittal angle of the medical device during the medical procedure;
   d) wirelessly communicating the data from the electrical component to the display device;
   e) displaying information related to the data to the user via the display device;
   f) repeating steps b) through e) as the medical device is moved relative to the subject until the medical procedure is complete; and
   g) removing the electrical component from the medical device.

13. The method of claim 12, and further comprising displaying instructions to the user, via the display device, to orient the medical device to a reference orientation associated with a stored reference medial and sagittal orientation.

14. The method of claim 12 and further comprising calibrating the medical device following step b), wherein calibrating the medical device includes aligning the medical device and storing a current orientation of the medical device as a reference orientation.

15. The method of claim 12, wherein the medical procedure is a spinal fusion.

16. The method of claim 12, wherein the medical device is one of a pedicle finder and a pedicle screwdriver.

17. The method of claim 12, wherein step c) includes detecting the medial angle and the sagittal angle via an inertial measuring unit of the electrical component.

18. The method of claim 12 and further comprising receiving a target orientation of the medical device and displaying on the display device with the information, at least one of: the target orientation and images of the subject obtained by at least one of fluoroscopy and a CT scan.

19. The method of claim 12 and further comprising generating a current through an electrically conductive portion of the medical device in response to a user input.

* * * * *